(12) United States Patent
George et al.

(10) Patent No.: US 10,760,566 B2
(45) Date of Patent: Sep. 1, 2020

(54) MAGNETICALLY DRIVEN PRESSURE GENERATOR

(71) Applicant: Nocira, LLC, Tempe, AZ (US)

(72) Inventors: David George, Scottsdale, AZ (US); Kevin E. Willey, Fort Collins, CO (US); John Claude, Redwood City, CA (US)

(73) Assignee: Nocira, LLC, Tempe, AZ (US)

( * ) Notice: Subject to any disclaimer, the term of this patent is extended or adjusted under 35 U.S.C. 154(b) by 553 days.

(21) Appl. No.: 15/657,039

(22) Filed: Jul. 21, 2017

(65) Prior Publication Data

US 2018/0023558 A1 Jan. 25, 2018

Related U.S. Application Data

(60) Provisional application No. 62/413,491, filed on Oct. 27, 2016, provisional application No. 62/365,874, filed on Jul. 22, 2016.

(51) Int. Cl.
| | |
|---|---|
| *F04B 49/06* | (2006.01) |
| *F04B 49/24* | (2006.01) |
| *F04B 43/04* | (2006.01) |
| *F04B 45/027* | (2006.01) |
| *G05B 15/02* | (2006.01) |
| *A61H 23/02* | (2006.01) |

(Continued)

(52) U.S. Cl.
CPC ............ *F04B 49/065* (2013.01); *A61F 11/00* (2013.01); *A61H 23/0218* (2013.01); *A61H 23/0236* (2013.01); *F04B 43/04* (2013.01); *F04B 45/027* (2013.01); *F04B 49/24* (2013.01); *G05B 15/02* (2013.01); *A61F 11/008* (2013.01); *F04B 51/00* (2013.01); *F04B 53/06* (2013.01)

(58) Field of Classification Search
CPC ...... F04B 49/065; F04B 43/04; F04B 45/027; F04B 49/24; F04B 51/00; F04B 53/06; A61H 23/0236; A61H 23/0218; A61F 11/00; A61F 11/008; G05B 15/02
See application file for complete search history.

(56) References Cited

U.S. PATENT DOCUMENTS

| | | |
|---|---|---|
| 841,146 A | 1/1907 | Hasbrouck |
| 2,176,366 A | 10/1939 | Smith |

(Continued)

FOREIGN PATENT DOCUMENTS

| | | |
|---|---|---|
| AU | 2004/238090 | 11/2004 |
| CA | 1136751 | 11/1982 |

(Continued)

OTHER PUBLICATIONS

European Patent Application No. 14816984.0; Office Action dated Nov. 24, 2017, 6 pages total.

(Continued)

*Primary Examiner* — Quang D Thanh
(74) *Attorney, Agent, or Firm* — Knobbe Martens Olson & Bear, LLP

(57) ABSTRACT

A magnetically driven pressure generator including a housing, flexible member, first magnetic force generator, and second magnetic force generator. The magnetically driven pressure generator oscillates the flexible member to increase or decrease the volume of a chamber, inversely increasing or decreasing the pressure of the chamber.

27 Claims, 15 Drawing Sheets

(51) Int. Cl.
*A61F 11/00* (2006.01)
*F04B 51/00* (2006.01)
*F04B 53/06* (2006.01)

(56) References Cited

U.S. PATENT DOCUMENTS

| | | |
|---|---|---|
| 2,437,490 A | 3/1948 | Watson et al. |
| 2,652,048 A | 9/1953 | Joers |
| 3,757,769 A | 9/1973 | Arguimbau et al. |
| 3,872,559 A | 3/1975 | Leight |
| 4,002,161 A | 1/1977 | Klar et al. |
| 4,133,984 A | 1/1979 | Akijama |
| 4,160,449 A | 7/1979 | Wade |
| 4,206,756 A | 6/1980 | Grossan |
| 4,244,377 A | 1/1981 | Grams |
| 4,289,143 A | 9/1981 | Canavesio et al. |
| 4,325,386 A | 4/1982 | Katz |
| 4,349,083 A | 9/1982 | Bennett |
| 4,472,342 A | 9/1984 | Carr |
| 4,552,137 A | 11/1985 | Strauss |
| 4,594,058 A * | 6/1986 | Fischell ............ A61M 5/14224 128/DIG. 12 |
| 4,632,104 A | 12/1986 | Conrow |
| 4,667,676 A | 5/1987 | Guinta |
| 4,688,582 A | 8/1987 | Heller et al. |
| 4,754,748 A | 7/1988 | Antowski |
| 4,757,807 A | 7/1988 | Densert et al. |
| 4,775,370 A | 10/1988 | Berry |
| 4,809,708 A | 3/1989 | Geisler et al. |
| 4,896,380 A | 1/1990 | Kamitani |
| 4,896,679 A | 1/1990 | St. Pierre |
| 4,964,769 A | 10/1990 | Hass |
| 4,984,579 A | 1/1991 | Burgert et al. |
| 5,024,612 A | 6/1991 | Van den Honert et al. |
| 5,105,822 A | 4/1992 | Stevens et al. |
| 5,131,411 A | 7/1992 | Casali et al. |
| 5,228,431 A | 7/1993 | Giarretto |
| 5,241,967 A | 9/1993 | Yasushi et al. |
| 5,421,818 A | 6/1995 | Arenberg |
| 5,476,446 A | 12/1995 | Arenburg |
| 5,483,027 A | 1/1996 | Krause |
| 5,483,975 A | 1/1996 | Hirschenbain |
| 5,488,961 A | 2/1996 | Adams |
| 5,631,965 A | 5/1997 | Chang et al. |
| 5,699,809 A | 12/1997 | Combs et al. |
| 5,740,258 A | 4/1998 | Goodwin-Johansson |
| 5,746,725 A | 5/1998 | Shalon et al. |
| 5,755,234 A | 5/1998 | Mobley et al. |
| 5,769,891 A | 6/1998 | Clayton |
| 5,776,179 A | 7/1998 | Ren et al. |
| 5,819,745 A | 10/1998 | Mobley et al. |
| 5,865,183 A | 2/1999 | Hirschebain |
| 5,868,682 A | 2/1999 | Combe et al. |
| 5,944,711 A | 8/1999 | Pender |
| 6,004,274 A | 12/1999 | Nolan et al. |
| 6,016,499 A | 1/2000 | Ferguson |
| 6,024,726 A | 2/2000 | Hill |
| 6,129,174 A | 10/2000 | Brown et al. |
| 6,139,507 A | 10/2000 | Jeng |
| 6,159,171 A | 12/2000 | Densert et al. |
| 6,186,959 B1 | 2/2001 | Canfield et al. |
| 6,258,067 B1 | 7/2001 | Hill |
| 6,296,652 B1 | 10/2001 | Qingmin |
| 6,359,993 B2 | 3/2002 | Birmhall |
| 6,430,443 B1 | 8/2002 | Karell |
| 6,511,437 B1 | 1/2003 | Nakamura et al. |
| 6,592,512 B2 | 7/2003 | Stökert et al. |
| 6,629,938 B1 | 10/2003 | Engvall et al. |
| 6,725,568 B2 | 4/2004 | Gronka |
| 6,748,275 B2 | 6/2004 | Lattner et al. |
| 6,800,062 B2 | 10/2004 | Epley |
| 6,820,717 B2 | 11/2004 | Fleming et al. |
| 6,878,128 B2 | 4/2005 | MacMahon et al. |
| 6,958,043 B2 | 10/2005 | Hissong |
| 6,981,569 B2 | 1/2006 | Stilp |
| 7,022,090 B1 | 4/2006 | Engvall et al. |
| 7,162,039 B1 | 1/2007 | Callahan |
| 7,179,238 B2 | 2/2007 | Hissong |
| 7,189,252 B2 | 3/2007 | Krueger |
| 7,268,466 B2 | 9/2007 | Rasmussen |
| 7,352,871 B1 | 4/2008 | Mozo |
| D570,457 S | 6/2008 | Brown |
| 7,613,519 B2 | 11/2009 | De Ridder |
| 7,766,858 B2 | 8/2010 | Franz et al. |
| 7,779,844 B2 | 8/2010 | Purcell et al. |
| 7,785,346 B2 | 8/2010 | Blumberg |
| 7,797,042 B2 | 9/2010 | Dietrich et al. |
| 7,833,282 B2 | 11/2010 | Mandpe |
| 7,892,180 B2 | 2/2011 | Epley |
| 7,959,597 B2 | 6/2011 | Baker et al. |
| 7,988,657 B2 | 8/2011 | Shapiro et al. |
| 8,020,563 B2 | 9/2011 | Pfanstiehl |
| 8,047,207 B2 | 11/2011 | Perez et al. |
| 8,052,693 B2 | 11/2011 | Shahoian |
| 8,122,892 B2 | 2/2012 | Johnson et al. |
| 8,142,373 B1 | 3/2012 | Riles |
| 8,199,919 B2 | 6/2012 | Goldstein et al. |
| 8,241,224 B2 | 8/2012 | Keefe |
| 8,249,285 B2 | 8/2012 | Killion et al. |
| 8,251,925 B2 | 8/2012 | Keady et al. |
| 8,262,717 B2 | 9/2012 | Rogers et al. |
| 8,267,983 B2 | 9/2012 | Rogers et al. |
| 8,267,984 B2 | 9/2012 | Rogers |
| 8,328,830 B1 | 12/2012 | Pandit |
| 8,398,562 B2 | 3/2013 | Keller |
| 8,414,521 B2 | 4/2013 | Baker et al. |
| 8,442,632 B2 | 5/2013 | Kullok et al. |
| 8,460,356 B2 | 6/2013 | Rogers et al. |
| 8,506,469 B2 | 8/2013 | Dietrich et al. |
| 8,515,552 B2 | 8/2013 | Englehart |
| 8,550,206 B2 | 10/2013 | Keady et al. |
| 8,568,348 B2 | 10/2013 | Vlodaver et al. |
| 8,603,152 B2 | 12/2013 | Smith et al. |
| 8,625,833 B1 | 1/2014 | Armwood |
| 8,666,502 B2 | 3/2014 | Hartlep et al. |
| 8,688,239 B2 | 4/2014 | Hartlep et al. |
| 8,696,724 B2 | 4/2014 | Rogers |
| 8,858,430 B2 | 10/2014 | Oyadiran et al. |
| 8,963,914 B2 | 2/2015 | Rawat et al. |
| 9,039,639 B2 | 5/2015 | George et al. |
| 9,168,171 B2 | 10/2015 | Rogers |
| 9,186,277 B2 | 11/2015 | George et al. |
| 9,283,111 B2 | 3/2016 | Rogers et al. |
| 9,526,653 B2 | 12/2016 | Rogers et al. |
| 9,532,900 B2 | 1/2017 | Smith et al. |
| 9,579,247 B2 | 2/2017 | Juto et al. |
| 9,655,772 B2 | 5/2017 | Smith et al. |
| 9,744,074 B2 | 8/2017 | Rogers |
| 9,849,026 B2 | 12/2017 | Rogers et al. |
| 10,076,464 B2 | 9/2018 | George et al. |
| 10,251,790 B2 | 4/2019 | George et al. |
| 10,271,992 B2 | 4/2019 | Hayahi et al. |
| 10,278,868 B2 | 5/2019 | George et al. |
| 2002/0069883 A1 | 6/2002 | Hirchenbain |
| 2003/0195588 A1 | 10/2003 | Fischell et al. |
| 2003/0220536 A1 | 11/2003 | Hissong |
| 2004/0097839 A1 | 5/2004 | Epley |
| 2004/0163882 A1 | 8/2004 | Fleming et al. |
| 2005/0065585 A1 | 3/2005 | Salas |
| 2005/0165460 A1 | 7/2005 | Erfan |
| 2005/0209516 A1 | 9/2005 | Fraden |
| 2005/0267388 A1 | 12/2005 | Hanna |
| 2006/0100681 A1 | 5/2006 | Salas Carpizo |
| 2006/0197412 A1 | 9/2006 | Rasmussen |
| 2006/0253087 A1 | 11/2006 | Vlodaver et al. |
| 2006/0272650 A1 | 12/2006 | Hoogenakker et al. |
| 2007/0040454 A1 * | 2/2007 | Freudenberger ........ F04B 43/04 310/12.04 |
| 2007/0060948 A1 | 3/2007 | Franz et al. |
| 2007/0112279 A1 | 5/2007 | Iseberg et al. |
| 2007/0250119 A1 | 10/2007 | Tyler et al. |
| 2007/0299362 A1 | 12/2007 | Epley et al. |
| 2008/0011308 A1 | 1/2008 | Fleming |
| 2008/0154183 A1 | 6/2008 | Baker et al. |

(56) References Cited

U.S. PATENT DOCUMENTS

| | | |
|---|---|---|
| 2008/0168775 A1 | 7/2008 | Windheim et al. |
| 2008/0208100 A1 | 8/2008 | Wolff |
| 2008/0212787 A1 | 9/2008 | Goldstein et al. |
| 2008/0220092 A1 | 9/2008 | Dipierro |
| 2008/0240942 A1* | 10/2008 | Heinrich .............. F04B 43/023 417/322 |
| 2008/0249439 A1 | 10/2008 | Tracey et al. |
| 2008/0264464 A1 | 10/2008 | Lee et al. |
| 2009/0012420 A1 | 1/2009 | Keller |
| 2009/0082831 A1 | 3/2009 | Paul et al. |
| 2009/0173353 A1 | 7/2009 | Pursell et al. |
| 2009/0182399 A1 | 7/2009 | Sylvestre |
| 2009/0228103 A1 | 9/2009 | Clayton |
| 2010/0002897 A1 | 1/2010 | Keady |
| 2010/0030131 A1 | 2/2010 | Morriss et al. |
| 2010/0071707 A1 | 3/2010 | Wohl |
| 2010/0071708 A1 | 3/2010 | Lenhardt |
| 2010/0113991 A1 | 5/2010 | Wu |
| 2010/0179490 A1 | 7/2010 | Connelly et al. |
| 2010/0198282 A1 | 8/2010 | Rogers |
| 2010/0211142 A1 | 8/2010 | Rogers |
| 2011/0079227 A1 | 4/2011 | Turcot et al. |
| 2011/0097141 A1 | 4/2011 | Brown |
| 2011/0098551 A1 | 4/2011 | Zhang |
| 2011/0130786 A1 | 6/2011 | Clayton et al. |
| 2011/0172739 A1 | 7/2011 | Mann et al. |
| 2011/0184341 A1 | 7/2011 | Baker et al. |
| 2011/0224493 A1 | 9/2011 | Oyadiran et al. |
| 2011/0245902 A1 | 10/2011 | Katz |
| 2012/0046607 A1 | 2/2012 | Syk |
| 2012/0203309 A1 | 8/2012 | Englehart |
| 2012/0265093 A1 | 10/2012 | Allen et al. |
| 2012/0296268 A1 | 11/2012 | Vlodaver et al. |
| 2012/0302859 A1 | 11/2012 | Keefe |
| 2012/0310077 A1 | 12/2012 | Rogers |
| 2012/0310313 A1 | 12/2012 | Rogers et al. |
| 2012/0318605 A1 | 12/2012 | Brown |
| 2013/0123889 A1 | 5/2013 | Katz et al. |
| 2013/0136285 A1 | 5/2013 | Naumann |
| 2013/0152949 A1 | 6/2013 | Simon |
| 2013/0177179 A1 | 7/2013 | Ambrose et al. |
| 2013/0183173 A1* | 7/2013 | Kohli .................... F04B 35/045 417/410.1 |
| 2013/0282070 A1 | 10/2013 | Cowan et al. |
| 2013/0303953 A1 | 11/2013 | Lattner |
| 2013/0304103 A1 | 11/2013 | Burres |
| 2013/0310907 A1 | 11/2013 | Rogers et al. |
| 2013/0324932 A1 | 12/2013 | Cogley |
| 2013/0331823 A1* | 12/2013 | Askem .................. F04B 45/047 604/543 |
| 2014/0069442 A1 | 3/2014 | Lewis et al. |
| 2014/0088671 A1 | 3/2014 | Rogers et al. |
| 2014/0243941 A1 | 8/2014 | Rogers et al. |
| 2014/0249608 A1 | 9/2014 | Rogers |
| 2014/0275827 A1 | 9/2014 | Gill et al. |
| 2014/0309715 A1 | 10/2014 | Smith et al. |
| 2014/0334652 A1 | 11/2014 | Gebert |
| 2015/0000678 A1 | 1/2015 | Buckler et al. |
| 2015/0005661 A1 | 1/2015 | Trammell |
| 2015/0141879 A1 | 5/2015 | Harper et al. |
| 2015/0320591 A1 | 11/2015 | Smith et al. |
| 2015/0320592 A1 | 11/2015 | Black et al. |
| 2015/0374538 A1 | 12/2015 | Rogers |
| 2016/0058620 A1 | 3/2016 | George et al. |
| 2016/0128897 A1 | 5/2016 | George et al. |
| 2016/0151206 A1 | 6/2016 | George et al. |
| 2016/0346117 A1 | 12/2016 | Rogers et al. |
| 2016/0378945 A1 | 12/2016 | Mian et al. |
| 2017/0105876 A1 | 4/2017 | O'Connell, Sr. et al. |
| 2017/0109988 A1 | 4/2017 | O'Connell, Sr. et al. |
| 2017/0135854 A1 | 5/2017 | Rogers et al. |
| 2017/0235889 A1 | 8/2017 | Main et al. |
| 2018/0000686 A1 | 1/2018 | George et al. |
| 2018/0008457 A1 | 1/2018 | Smith et al. |
| 2018/0106244 A1* | 4/2018 | Wang ..................... F04B 17/03 |
| 2018/0125748 A1* | 5/2018 | Goldenberg .......... F04B 49/022 |
| 2019/0231597 A1 | 8/2019 | Sullivan |
| 2020/0121544 A1 | 4/2020 | George et al. |

FOREIGN PATENT DOCUMENTS

| | | |
|---|---|---|
| CA | 1222464 | 6/1987 |
| CA | 1241152 | 8/1988 |
| CA | 2003452 | 6/1990 |
| CA | 2275057 | 10/1999 |
| CA | 2 337 076 | 1/2000 |
| CA | 2429560 | 1/2004 |
| CN | 2075517 U | 4/1991 |
| CN | 2418864 | 2/2001 |
| CN | 1308513 A | 8/2001 |
| CN | 2530645 | 1/2003 |
| CN | 2912525 | 6/2007 |
| CN | 200945215 Y | 9/2007 |
| CN | 201143258 | 11/2008 |
| CN | 201164541 | 12/2008 |
| CN | 101668497 | 3/2010 |
| CN | 201505220 U | 6/2010 |
| CN | 201524178 | 7/2010 |
| CN | 201558360 | 8/2010 |
| CN | 201870809 | 6/2011 |
| CN | 202036187 | 11/2011 |
| CN | 202185057 | 4/2012 |
| CN | 102484761 | 5/2012 |
| CN | 102551957 | 7/2012 |
| CN | 202313927 | 7/2012 |
| CN | 102647966 | 8/2012 |
| CN | 202477966 | 10/2012 |
| CN | 202505833 | 10/2012 |
| CN | 102986250 | 3/2013 |
| DE | 102011008802 | 7/2012 |
| EP | 0026247 | 4/1981 |
| EP | 0400900 | 12/1990 |
| EP | 1027863 | 8/2000 |
| EP | 2207366 | 7/2010 |
| EP | 2990017 | 3/2016 |
| FR | 2 605 516 A1 | 4/1988 |
| GB | 1432572 | 4/1976 |
| GB | 1522031 | 8/1978 |
| GB | 2054387 | 2/1981 |
| GB | 2185688 | 7/1987 |
| GB | 2343263 | 5/2000 |
| GB | 2479891 | 11/2011 |
| IT | 1214840 | 1/1990 |
| JP | S 57-188245 | 11/1982 |
| JP | H 07-111987 | 5/1995 |
| JP | 2006345903 | 12/2006 |
| JP | 2009022699 | 2/2009 |
| JP | 2010233643 | 10/2010 |
| JP | 2010233643 | 12/2010 |
| JP | 2011217986 | 11/2011 |
| JP | 2013068448 | 4/2013 |
| JP | 2013102784 | 5/2013 |
| KR | 10-1273296 | 6/2013 |
| MX | 9705652 | 7/1998 |
| MX | PA03005598 | 10/2004 |
| MX | 2010014470 | 2/2011 |
| MX | 2011006854 | 8/2011 |
| MX | 2012007726 | 8/2012 |
| WO | 86/01399 | 3/1986 |
| WO | WO 94/22372 | 10/1994 |
| WO | WO 1996/23293 | 8/1996 |
| WO | 97/23178 | 7/1997 |
| WO | 2000/001331 | 1/2000 |
| WO | 2000/001346 | 1/2000 |
| WO | 2000/010484 | 3/2000 |
| WO | WO 00/10627 | 3/2000 |
| WO | WO 2000/010848 | 3/2000 |
| WO | WO 03/075761 | 9/2003 |
| WO | WO 2004/064672 | 8/2004 |
| WO | 2004/100844 | 11/2004 |
| WO | WO 2004/100844 | 11/2004 |
| WO | WO 2006/009545 | 1/2006 |
| WO | WO 2007/084674 | 7/2007 |
| WO | WO 2007/118092 | 10/2007 |

(56) References Cited

FOREIGN PATENT DOCUMENTS

| WO | WO 2007/145853 | 12/2007 |
|----|----|----|
| WO | WO 2008/036368 | 3/2008 |
| WO | WO 2008/064230 | 5/2008 |
| WO | WO 2008/086187 | 7/2008 |
| WO | WO 2008/128173 | 10/2008 |
| WO | WO 2008/153588 | 12/2008 |
| WO | WO 2009/020862 | 2/2009 |
| WO | WO 2009/050306 | 4/2009 |
| WO | WO 2009/077902 | 6/2009 |
| WO | WO 2009/077902 | 10/2009 |
| WO | WO 2010/005899 | 1/2010 |
| WO | WO 2010/016925 | 2/2010 |
| WO | WO 2010/085196 | 7/2010 |
| WO | WO 2011/075573 | 6/2011 |
| WO | WO 2011/075574 | 6/2011 |
| WO | 2012/007193 | 1/2012 |
| WO | WO 2012/083098 | 6/2012 |
| WO | WO 2012/083102 | 6/2012 |
| WO | WO 2012/083106 | 6/2012 |
| WO | WO 2012/083126 | 6/2012 |
| WO | WO 2012/083151 | 6/2012 |
| WO | WO 2013/075255 | 5/2013 |
| WO | WO 2014/120947 | 8/2014 |
| WO | WO 2014/210457 | 12/2014 |
| WO | WO 2015/009421 | 1/2015 |
| WO | 2015/074060 | 5/2015 |
| WO | WO 2016/022761 | 2/2016 |
| WO | WO 2017/040739 | 3/2017 |
| WO | WO 2017/040741 | 3/2017 |
| WO | WO 2017/040747 | 3/2017 |
| WO | WO 2017/197150 | 11/2017 |
| WO | WO 2018/157143 | 8/2018 |
| WO | WO 2019/246456 | 12/2019 |
| ZA | 200509787 | 1/2009 |

OTHER PUBLICATIONS

Sullivan: "Ear Insufflation as a Novel Therapy Which Produces Rapid Relief of Migraine Headache—a Case Study," Funct Neurol Rehabil Egon 2013; vol. 3, Issue 1, pp. 93-107. Published on Jun. 7, 2013. Revised Jan. 28, 2013. Accepted Feb. 15, 2013.
Sullivan: "Ear Insufflation Produces Rapid and Significant Relief of Trigeminal Neuraliga," Funct Neurol Rehabil Egon 2013; vol. 3, Issue 4, pp. 1-6. Published on May 26, 2014. Revised Dec. 24, 2013. Accepted Jan. 12, 2014.
Transcript of News Story, Aug. 22, 2013, video available at: https://www.facebook.com/178787878873891/videos/10201196245541704/.
"New Migraine Therapy," Aug. 22, 2013, video available at https://www.facebook.com/178787878873891/videos/10201196245541704/.
Transcript of News Story, Nov. 13, 2013, video available at: https://www.facebook.com/178787878873891/videos/treatment-for-migraines-and-trigeminal-neuralgia/10201781732138503/.
"Revolutionary Pain Therapy," Nov. 13, 2013, video available at https://www.facebook.com/178787878873891/videos/treatment-for-migraines-and-trigeminal-neuralgia/10201781732138503/.
Transcript of News Story, Jul. 7, 2014, video available at: https://www.facebook.com/178787878873891/videos/681870651898942/.
"New Therapy for Migraines," Jul. 7, 2014, video available at https://www.facebook.com/178787878873891/videos/treatment-for-migraines-and-trigeminal-neuralgia/10201781732138503/.
Transcript of Webinar, Apr. 10, 2013, video available at: https://www.anymeeting.com/WebConference/RecordingDefault.aspx?c_psrid=ED57DC868548.
"A novel application to resolve migraine headaches—A Functional Neurology forum," Apr. 10, 2013, video available at: https://www.anymeeting.com/WebConference/RecordingDefault.aspx?c_psrid=ED57DC868548.
International Search Report and Written Opinion in co-pending application No. PCT/US2018/019981, dated Jun. 27, 2018 in 15 pages.

Breathometer. Breathometer—The World's First Smartphone Breathalyzer. Website, http://www.breathometer.co, originall downloaded Jun. 19, 2014, 8 total pages.
Cadwell. Sierra Wave. Website, http://www.cadwell.com, originally downloaded Feb. 27, 2014, 1 page.
Ferrotec. Thermal Solutions. Website, https://thermal.ferrotec.com, originally downloaded Feb. 27, 2014, 1 page.
Ferrotec. Thermoelectric Technical Reference—Installation of Thermoelectric Modules. Website, https://thermal.ferrotec.com, originally downloaded May 21, 2014, 4 total pages.
Ferrotec. Thermoelectric Technical Reference—Introduction to Thermoelectric Cooling. Website, https://www.ferrotec.com, originally downloaded Feb. 27, 2014, 2 total pages.
Kolev. How caloric vestibular irrigation influences migraine attacks. Cephalalgia. Aug. 1990, vol. 10, Issue 4, pp. 167-169 (abstract only).
Lifting the Burden. The Global Campaign Against Headache. Website, http://www.l-t-b.org, originally downloaded Feb. 27, 2014, 1 page.
Liszewski. Ear Pressure Equalizer. Website, http://www.ohgizmo.com, originally downloaded Dec. 18, 2013, 1 page.
Long Island NEWS12.Com. Long Island Naturally: Migraines. Website video, http://longisland.news12.com, originally downloaded Nov. 26, 2013, 3 total pages.
Medscape. Peripheral Nerve Stimulator—Train of Four Monitoring. Website, http://emedicine.medscape.com, originally downloaded Feb. 27, 2014, 2 total pages.
Medtronic. Meniett Device for Meniere's Disease. Meniett Low-Pressure Pulse Generator device. Website, http://www.medtronic.com, originally downloaded Feb. 27, 2014, 2 pages.
New York Health Solutions. Migraine Headaches. Website, http://www.nyhealthsolutions.com, originally downloaded May 23, 2014, 2 total pages.
Pietrobon. Migraine: new molecular mechanisms. Neuroscientist. Aug. 2005, vol. 11, issue 4, pp. 373-386 (abstract only).
Saunders. Tympanic membrane sensation. Brain. Jun. 1985, vol. 108, Issue 6, pp. 387-404 (abstract only).
Sheftell, et al. Harry Potter and the Curse of Headache. Headache: The Journal of Head and Face Pain. Jun. 2007, vol. 47, issue 6, pp. 911-916 (abstract only).
Smartproducts. Series 100—Cartridge Specialty Check Valves and Pressure Relief Valves. Online catalog, www.smartproducts.coom, originally downloaded Mar. 28, 2014, 2 pages.
Stovner, et al. The global burden of headache: a documentation of headache prevalence and disability worldwide. Cephalalgia, 2007, vol. 27, pp. 193-210.
Sullivan. Ear Insufflation as a Novel Therapy Which Produces Rapid Relief of Migraine Headache. Funct Neurol Rehabil Egon, 2013, 3(1):93-107.
Sullivan. Ear Insufflation Produces Rapid and Significant Relief of Trigeminal Neuraliga. Funct Neurol Rehabil Egon, 2013, 3(4):1-6.
Ultimate Ears. Ultimate Ears Custom In-Ear Monitors. Website, http://pro.ultimateears.com, originally downloaded Feb. 27, 2014, 3 total pages.
Westone. Occupational Earpieces. Website, http://www.westone.com, originally downloaded Feb. 27, 2014, 2 total pages.
Wikipedia. Microcurrent electrical neuromuscular stimulator. Website, http://en.wikipedia.org, originally downloaded Feb. 27, 2014, 3 total pages.
Wikipedia. Somatosensory evoked potential. Website, http://en.wikipedia.org, originally downloaded Feb. 27, 2014, 5 total pages.
Wikipedia. Transcutaneous electrical nerve stimulation. Website, http://en.wikipedia.org, originally downloaded Feb. 27, 2014, 5 total pages.
World Health Organization. Headache disorders. Website, http://www.who.int, originally downloaded Feb. 27, 2014, 4 total pages.
U.S. Appl. No. 61/983,865, filed Apr. 24, 2014.
U.S. Appl. No. 61/863,317, filed Aug. 7, 2013.
Patent Cooperation Treaty Patent Application No. PCT/US14/44159, filed Jun. 25, 2014.
U.S. Appl. No. 14/292,469, filed May 30, 2014.
U.S. Appl. No. 14/936,332, filed Nov. 9, 2015.

(56) References Cited

OTHER PUBLICATIONS

U.S. Appl. No. 62/413,491, filed Oct. 27, 2016.
U.S. Appl. No. 62/365,874, filed Jul. 22, 2016.
George et al. Safety and usability factors in development of a novel, automated treatment device for acute migraine. Biomedical sciences instrumentation. Biomedical sciences instrumentation, Jan. 2017, 53, pp. 398-403.
Chinese Patent Application No. 201480042665.7; Office Action dated Sep. 4, 2017, 6 pages total.
Akerman et al. Pearls and pitfalls in experimental invivo models of migraine: Dural trigeminovascular nociception. Cephalagia, 2013, 33 (8), pp. 557-592.
Baguley et al. Does caloric vestibular stimulation modulate tinnitus? Neuroscience Letters, Mar. 2011, 492(1), pp. 52-54.
Baier et al. Vestibular-Evoked Myogenic Potentials in "Vestibular Migraine" and Meniere's Disease. Ann. N.Y. Acad. Sci., May 2009, 1164, pp. 324-327.
Becker. Weather and migraine: Can so many patients be wrong? Cephalalgia, Mar. 2011, 31(4), pp. 387-390.
Bolay et al. Does Low Atmospheric Pressure Independently Trigger Migraine? Headache, Oct. 2011, 51(9), pp. 1426-1430.
Dasilva et al. tDCS-Induced Analgesia and Electrical Fields in Pain-Related Neural Networks in Chronic Migraine. The Journal of Head and Face Pain, Sep. 2012, 52, pp. 1283-1295.
Dirckx et al. Human tympanic membrane deformation under static pressure. Hearing Research, Jan. 1991, 51(1), pp. 93-105.
Facebook. ZōK:The first migraine and headache solution. Webpage, https://www.facebook.com, originally downloaded May 18, 2017, 10 pages total.
Fasold et al. Human Vestibular Cortex as Identified with Caloric Stimulation in Functional Magnetic Resonance Imaging. NeuroImage, Nov. 2002, 17(3), pp. 1384-1393.
Hu et al. Burden of migraine in the United States: disability and economic costs. Arch. Intern. Med., Apr. 1999, 159, pp. 813-818.
Janetta. Neurovascular Compress in Cranial Nerve and Systemic Disease. Ann Surg, Oct. 1980, 192(4), pp. 518-524.
Job et al. Cortical Representation of Tympanic Membrane Movements due to Pressure Variation: An fMRI Study. Human Brain Mapping, May 2011, 32(5), pp. 744-749.
Kickstarter. ZōK: The first headache product that solves migraines and headaches. Website, http://www.funded.today, originally downloaded May 18, 2017, 3 pages total.
Klingner et al. Components of vestibular cortical function. Behavioral Brain Research, Jan. 2013, 236(1), pp. 194-199.
McGeoch et al. Vestibular stimulation can relieve central pain of spinal origin. Spinal Cord, Nov. 2008, 46(11), pp. 756-757.
Medtronic. The Meniett Device for Meniere's Disease. On-line article, http://www.medtronic.com, originally downloaded Mar. 13, 2015, 2 total pages.
Meng et al. Migraine Prevention with a Supraorbital Transcutaneous Stimulator: A Randomized Controlled Trial. Neurology, Sep. 2013, 81, pp. 1102-1103.
Minen. Tinnitus and Headache. American Migraine Foundation, website, downloaded Feb. 8, 2017, 3 pages total.
Mosqueria et al. Vagus Nerve Stimulation in Patients with Migraine. Rev Neurol, 2013, 57(2), English Abstract.
Nagai et al. Encapsulated nerve corpuscles in the human tympanic membrane. Archives of Otorhinolaryngology, 1989, 246(3), pp. 169-172.
Nihashi et al. Representation of the ear in human primary somatosensory cortex. NeuroImage, Feb. 2001, 13(2), pp. 295-304 (abstract only).
Olesen et al. Emerging Migraine treatments and drug targets. Trends in Pharmacological Sciences, 2011, 32(6), pp. 352-359.
Pasadena Pain Masnagement. Easing Migraine Symptoms with a Simple Puff of Air into the Ear; article by Dr. Stender. Website, http://www.pasadenapainmanagement.com, originally downloaded Apr. 25, 2016, 5 pages total.
Pedersen et al. Neurostimulation in cluster headache: A review of current progress. Cephalagia, 2013, 33(14), pp. 1179-1193.
Porta-Etessam et al. Neuro-otological symptoms in patients with migraine. Neurologia, Mar. 2011, 26(2), pp. 100-104.
Ramachandran et al. Rapid Relief of Thalamic Pain Syndrome Induced by Vestibular Caloric Stimulation. Neurocase, Jun. 2007, 13(3), pp. 185-188.
Sakata et al. Air pressure-sensing ability of the middle ear—Investigation of sensing regions and appropriate measurement conditions. Auris Nasus Larynx, Aug. 2009, 36(4), pp. 393-399.
Sameiro-Barbosa et al. Sensory Entrainment Mechanisms in Auditory Perception: Neural Synchronization Cortico-Striatal Activation. Frontiers in Neuroscience, Aug. 2016, vol. 10, Article 361, 8 pages.
Schoenen et al. Migraine prevention with a supraorbital transcutaneous stimulator. Neurology, 2013, 80(8), pp. 697-704.
Schulman. Breath-Holding, Head Pressure, and Hot Water: An Effective Treatment for Migraine Headache. Headache, Nov.-Dec. 2002, 42(10), pp. 1048-1050.
Scion Neurostim. Therapeutic Neuromodulation via Caloric Vestibular Stimulation. Thermoneuromodulation (TNM). Slides for presentation, dated Sep. 2015, 12 pages total.
Silberstein et al. Botulinum Toxin Type A as a Migraine Preventive Treatment. The Journal of Head and Face Pain, Jun. 2000, 40, pp. 445-450.
Smile Columbia Dentistry. Let Me Blow in Your Ear, for Migraine Treatment, of Course; article by Dr. Adam Hahn. Website, https://www.tmjtreatmentsc.com, originally downloaded Apr. 25, 2016, 2 pages total.
Mayr. The Origins of Feedback Control. M.I.T. Press, 1970.
U.S. Appl. No. 07/286,744, filed Dec. 19, 1988.
U.S. Appl. No. 61/905,616, filed Nov. 18, 2013.
Patent Cooperation Treaty International Patent Application No. PCT/US2014/066191; Written Opinion of the International Searching Authority dated Feb. 26, 2015, 7 pages total.
U.S. Appl. No. 14/980,226, filed Dec. 28, 2015.
Corresponding New Zealand Patent Application No. 713887; Office Action dated Jul. 13, 2016, 8 pages total.
Corresponding European Patent Application No. 14816984.0; Office Action dated Dec. 8, 2016, 9 pages total.
Chinese Patent Application No. 201480042665.7; Office Action dated Jan. 22, 2017, 26 pages total.
Corresponding New Zealand Patent Application No. 713887; Office Action dated Feb. 20, 2017, 9 pages total.
Corresponding New Zealand Patent Application No. 713887; Office Action dated Jun. 7, 2017, 9 pages total.
Berthold Langguth, Verena Hund, Volker Busch, et al., "Tinnitus and Headache," BioMed Research International, vol. 2015, Article ID 797416, 7 pages, 2015. https://doi.org/10.115/2015/797416 (Year: 2015) in 7 pages.
Cathcart, et al., "Pain sensitivity mediates the relationship between stress and headache intensity in chronic tension-type headache", Nov. 2012 (Year: 2012) in 5 pages.
Cranial Nerves—Wikipedia, https://en.wikipedia.org/aiki/Cranial_nerves, printed Aug. 16, 2019 in 12 pages.
Croley, Christen, "Mechanicsburg doctor develops new migraine therapy," The Sentinel, Nov. 9. 2012.
Doherty, Colleen. "The Link Between Migraines and Tinnitus". Verywell Health, Nov. 23, 2019, https://www.verywellhealth.com/link-between-migraines-and-tinnitus-4077631#citation-10 (Year: 2019) in 4 pages.
Frangos E, Ellrich J, Komisaruk B. Non-invasive access to the vagus nerve central projections via electrical stimulation of the external ear: fMRI evidence in humans. Brain Stimul. Dec. 6, 2014. 8(3), 624-636 in 13 pages.
Kanzara T, Hall A, Virk J, Leung B, Singh A. Clinical anatomy of the tympanic nerve: A review. World J Otorhinolaryngol. Nov. 2014; 4(4), 17-22 in 8 pages.
Kiyokawa J., Yamaguchi K, Okada R, Maehara T, Akita K. Origin, course and distribution of the nerves to the posterosuperior wall of the external acoustic meatus. Anat Sci Int. Mar. 2014; 89(4), 238-245.
Saunders R, Tympanic membrane sensation. Brain. 1985, 108, 378-404 in 18 pages.

(56) References Cited

OTHER PUBLICATIONS

Shevel, "Headaches and tinnitus: correlation found", May 2008 (Year: 2006).

Tekdemir I, Aslan A, Elhan A., A clinico-anatomic study of the auricular branch of the vagus nerve and Arnold's ear-cough reflex. Surg Raiol Anat. 1998. 20(4), 253-257 in 5 pages.

Tekdemir I, Aslan A, Tuccar E, He C, Elhan A, Deda H. An anatomical study of the tympanic branch of the glossopharyngeal nerve (nerve of Jacobson). Ann Anat. Aug. 1998; 180(4): 349-52 in 4 pages.

Von Korff, et al., "Assessing headaches severity. New Directions", Jul. 1994 (Year: 1994).

Widemar L, Hellstrom S, Schultzberg M, Stenfors LE. Autonomic innervation of the tympanic membrane. An immunocytochemical and histofluorescence study. Acta Otolaryngol. Jul.-Aug. 1985;100(1-2):58:65 in 9 pages.

U.S. Appl. No. 61/841,111, filed Jun. 28, 2013.

\* cited by examiner

MAGNETICALLY DRIVEN PRESSURE GENERATOR

This U.S. Non-Provisional patent application claims the benefit of U.S. Provisional Patent Application No. 62/413,491, filed Oct. 27, 2016, and U.S. Provisional Patent Application No. 62/365,874, filed Jul. 22, 2016, each hereby incorporated by reference herein.

TECHNICAL FIELD

A magnetically driven pressure generator operable to adjust fluid pressure of an amount of fluid in an enclosed space to match pre-selected amplitude or frequency values or generate a continuous or intermittent fluid flow of the amount of fluid from the enclosed space to match pre-selected fluid pressure or fluid flow rate values over a period of time.

SUMMARY OF THE INVENTION

A broad object of the invention can be to provide a magnetically driven pressure generator, including one or more of: a housing having an open end and a closed end, a flexible member having a peripheral margin sealably coupled to the open end to define an enclosed space, a first magnetic force generator disposed on the flexible member, and a second magnetic force generator disposed proximally adjacent to the flexible member, where either the first magnetic force generator or second magnetic force generator comprises an electromagnetic force generator, and a controller configured to continuously or intermittently control the magnitude and direction of a current flowing in the electromagnetic force generator to correspondingly continuously or intermittently control amplitude and frequency of flexure of the flexible member, to decrease or increase the volume of the enclosed space to correspondingly increase or decrease pressure within the enclosed space, or to correspondingly generate fluid flow in an amount of fluid.

Another broad object of the invention can be a method of making a magnetically driven pressure generator, including sealably engaging a peripheral margin of a flexible member to an open end of a housing, disposing a first magnetic force generator on the flexible member, disposing a second magnetic force generator proximate to the open end or the closed end of the housing, where either the first magnetic force generator or second magnetic force generator comprises an electromagnetic force generator, and providing a controller configured to continuously or intermittently control the magnitude and direction of a current flowing in the electromagnetic force generator to correspondingly intermittently or continuously control amplitude and frequency of flexure of the flexible member to correspondingly decrease or increase the volume of a closed space, to correspondingly increase or decrease pressure within the enclosed space, or to correspondingly generate fluid flow in an amount of fluid.

Another broad object of the invention can be a method of using a magnetically driven pressure generator, including obtaining a magnetically driven pressure generator, including a housing, a flexible member, a first magnetic force generator disposed on the flexible member, and a second magnetic force generator disposed proximally adjacent the flexible member, where either the first magnetic force generator or second magnetic force generator comprises an electromagnetic force generator operable to generate an amount of flexure of the flexible member to decrease or increase the volume of a closed space, pre-selecting the amplitude and frequency of a pressure change in the closed space by configuring a controller to correspondingly continuously or intermittently control the magnitude and direction of a current flowing in the electromagnetic force generator to correspondingly generate an amount of flexure of the flexible member to decrease or increase the volume of a closed space to continuously or intermittently generate the pre-selected amplitude and frequency in the closed space.

Naturally, further objects of the invention are disclosed throughout other areas of the specification, drawings, photographs, and claims.

A BRIEF DESCRIPTION OF THE DRAWINGS

DETAILED DESCRIPTION OF THE PREFERRED EMBODIMENTS

Figure 2:
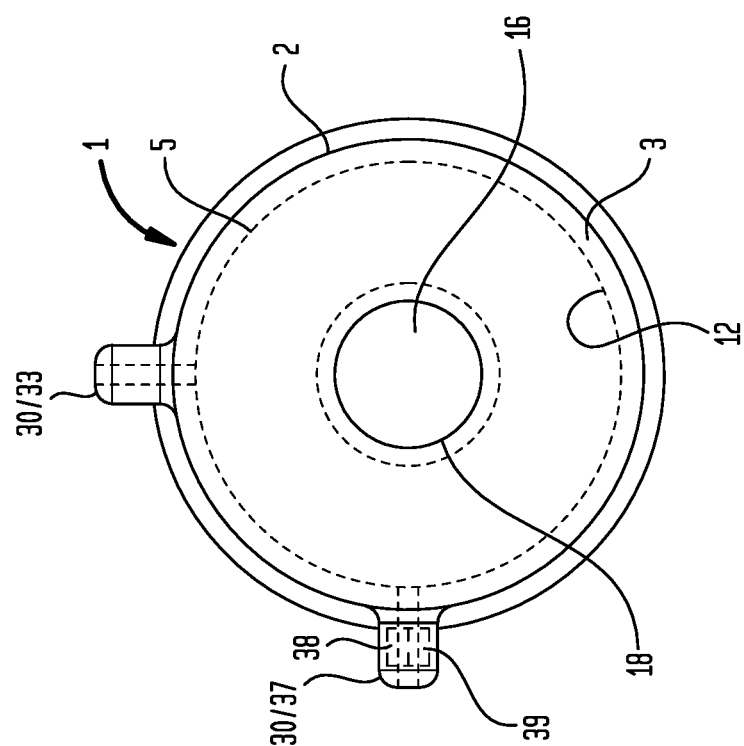
FIG. 2 is a front view of an embodiment of the magnetically driven pressure generator.

Referring generally to FIGS. 1 through 25, particular embodiments of a magnetically driven pressure generator (1) can include one or more of: a housing (2) having an open end (3) and a closed end (4), a flexible member (5) having a peripheral margin (6) sealably coupled to the open end (3) of said housing (2), a first magnetic force generator (7) disposed on the flexible member (5), and a second magnetic force generator (8) disposed proximally adjacent the flexible member (5), where either the first magnetic force generator (7) or second magnetic force generator (8) comprises an electromagnetic force generator (9).

Figure 1:
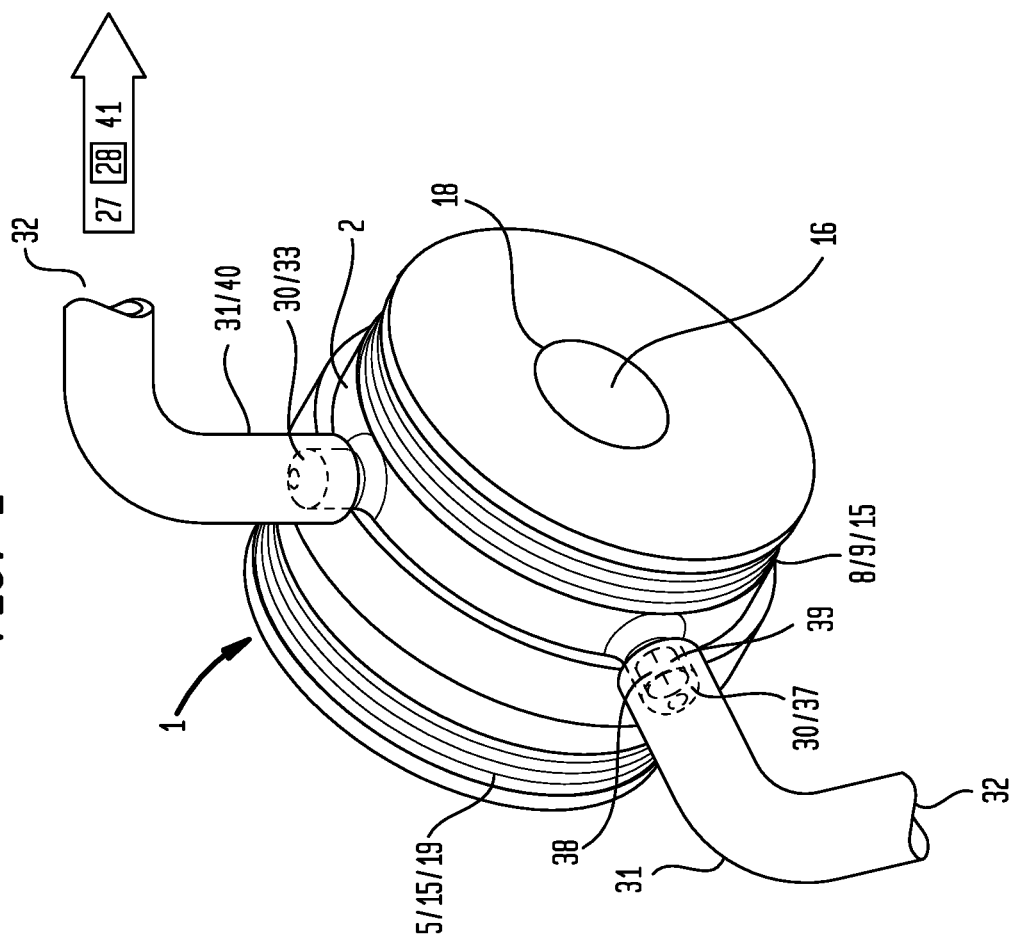
FIG. 1 is a perspective view of an embodiment of the magnetically driven pressure generator.
Figure 3:
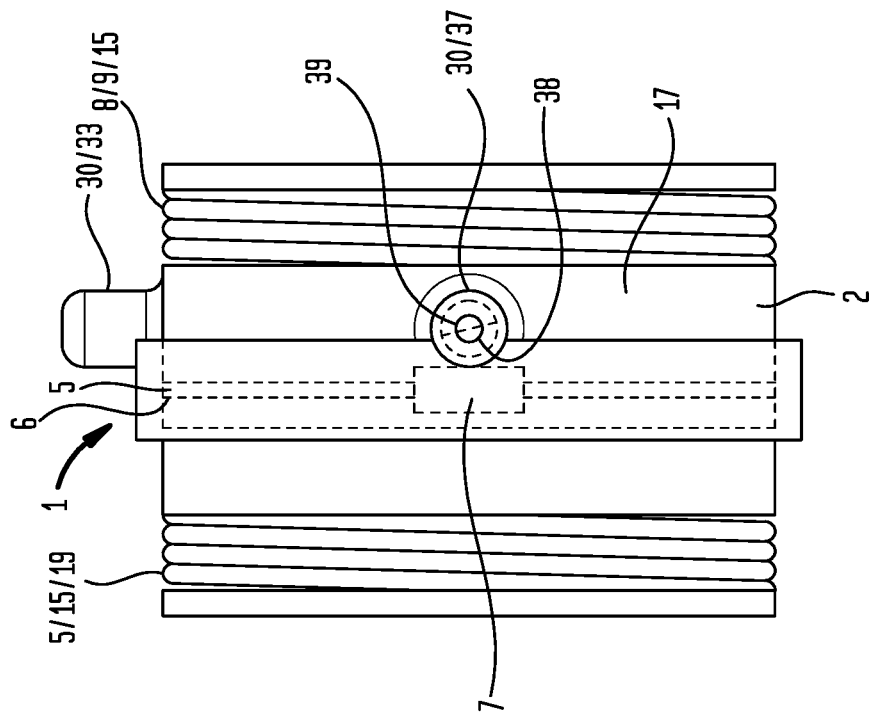
FIG. 3 is a top view of an embodiment of the magnetically driven pressure generator.
Figure 4:
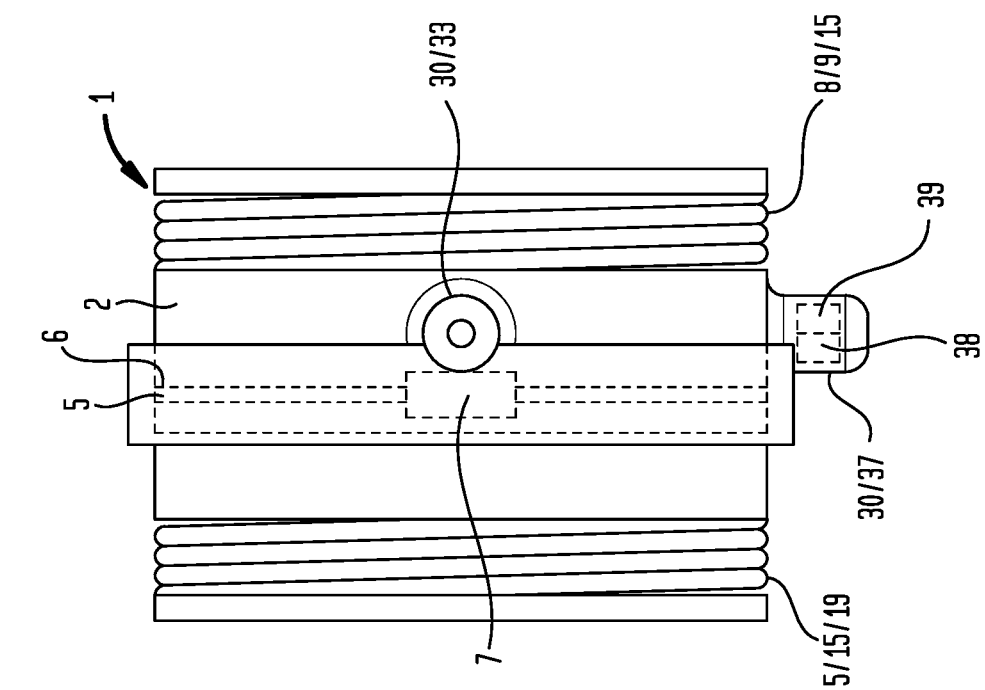
FIG. 4 is a side view of an embodiment of the magnetically driven pressure generator.
Figure 5:
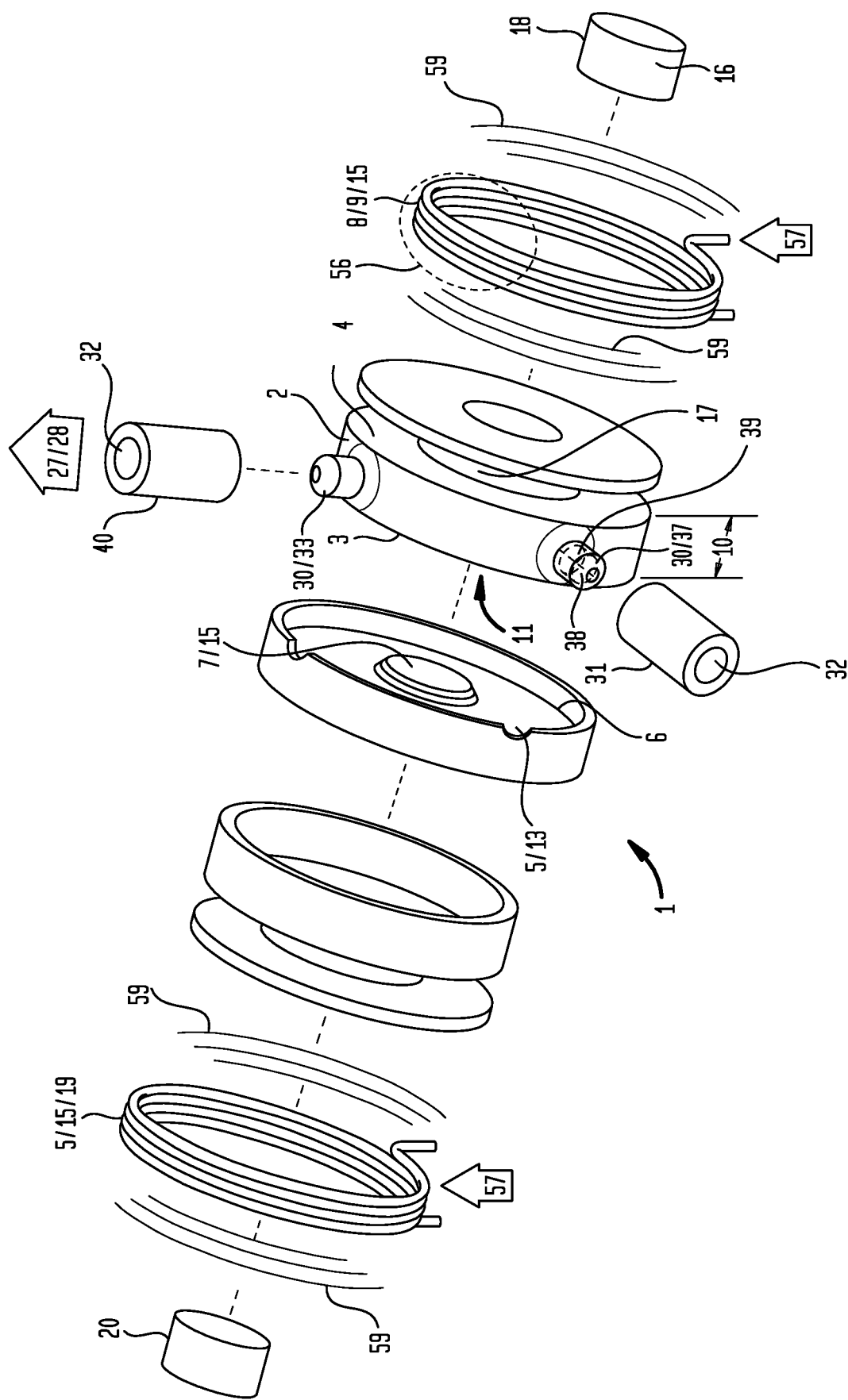
FIG. 5 is an exploded view of an embodiment of the magnetically driven pressure generator.
Figure 6:
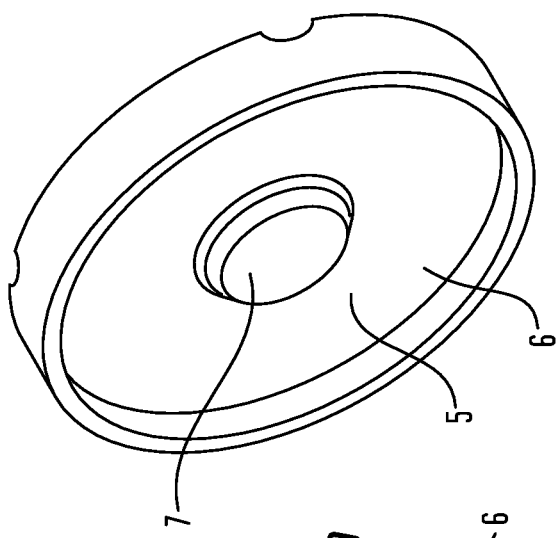
FIG. 6 is a perspective view of an embodiment of the flexible member.
Figure 9:
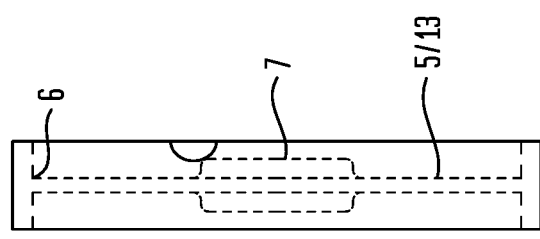
FIG. 9 is a side view of an embodiment of the flexible member.
Figure 7:
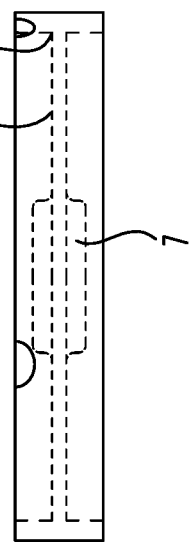
FIG. 7 is a top view of an embodiment of a flexible member.
Figure 8:
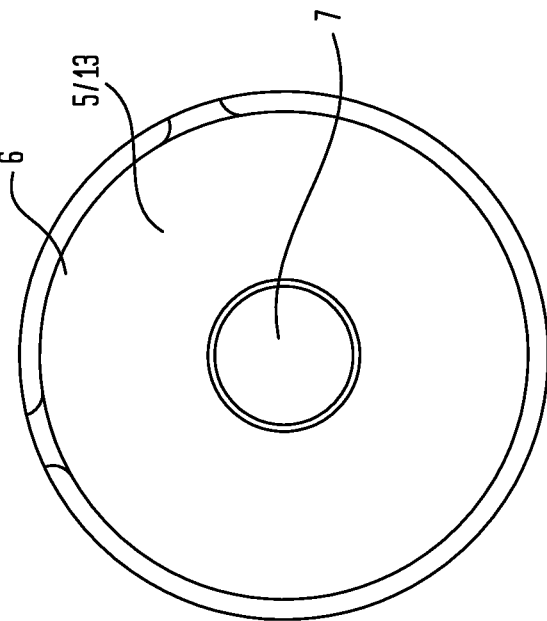
FIG. 8 is a front view of an embodiment of the flexible member.
Figure 10:
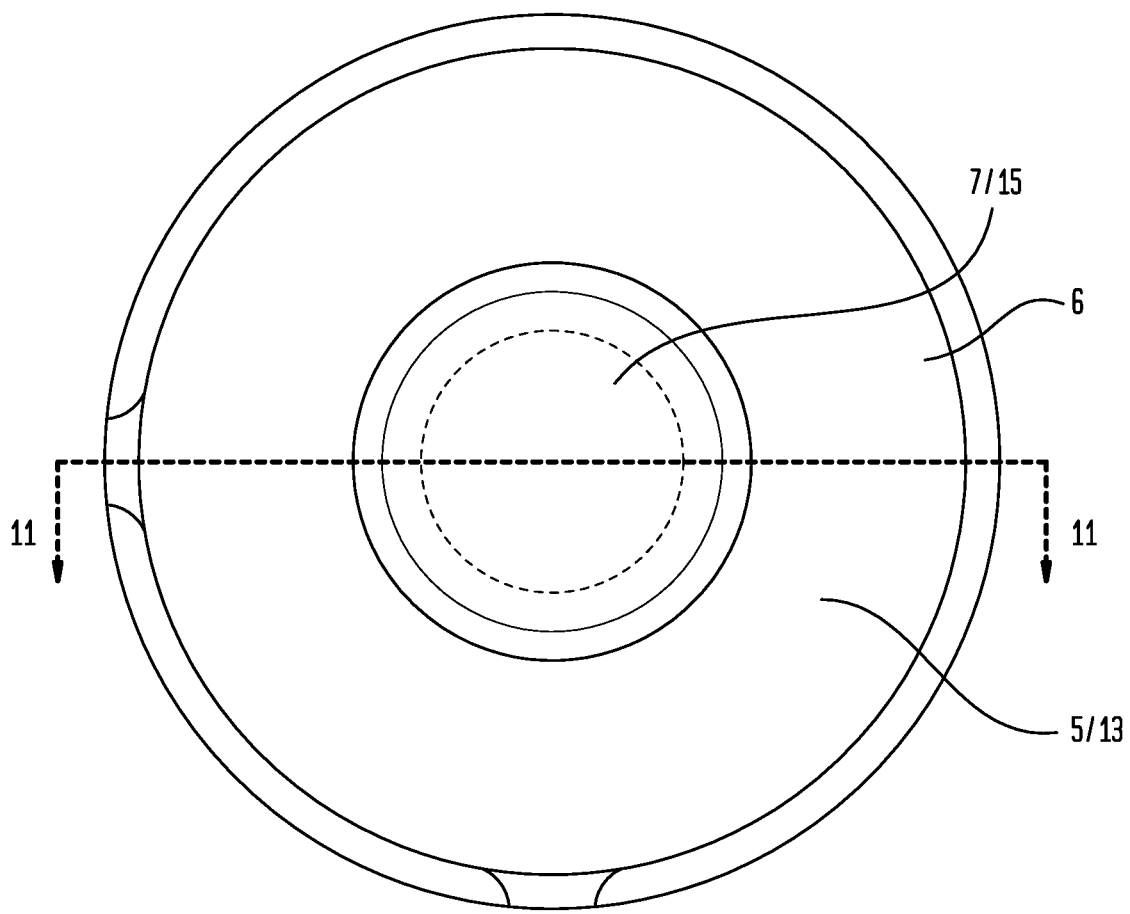
FIG. 10 is a front view of an embodiment of the flexible member including a magnet as a first magnetic force generator.
Figure 11:
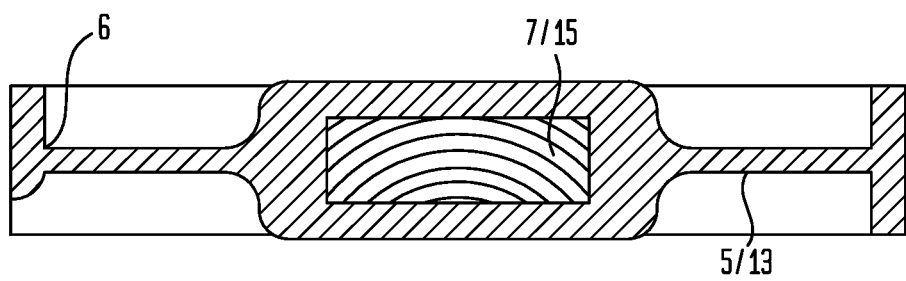
FIG. 11 is a cross section 11-11 of the flexible member shown in FIG. 10.
Figure 12:
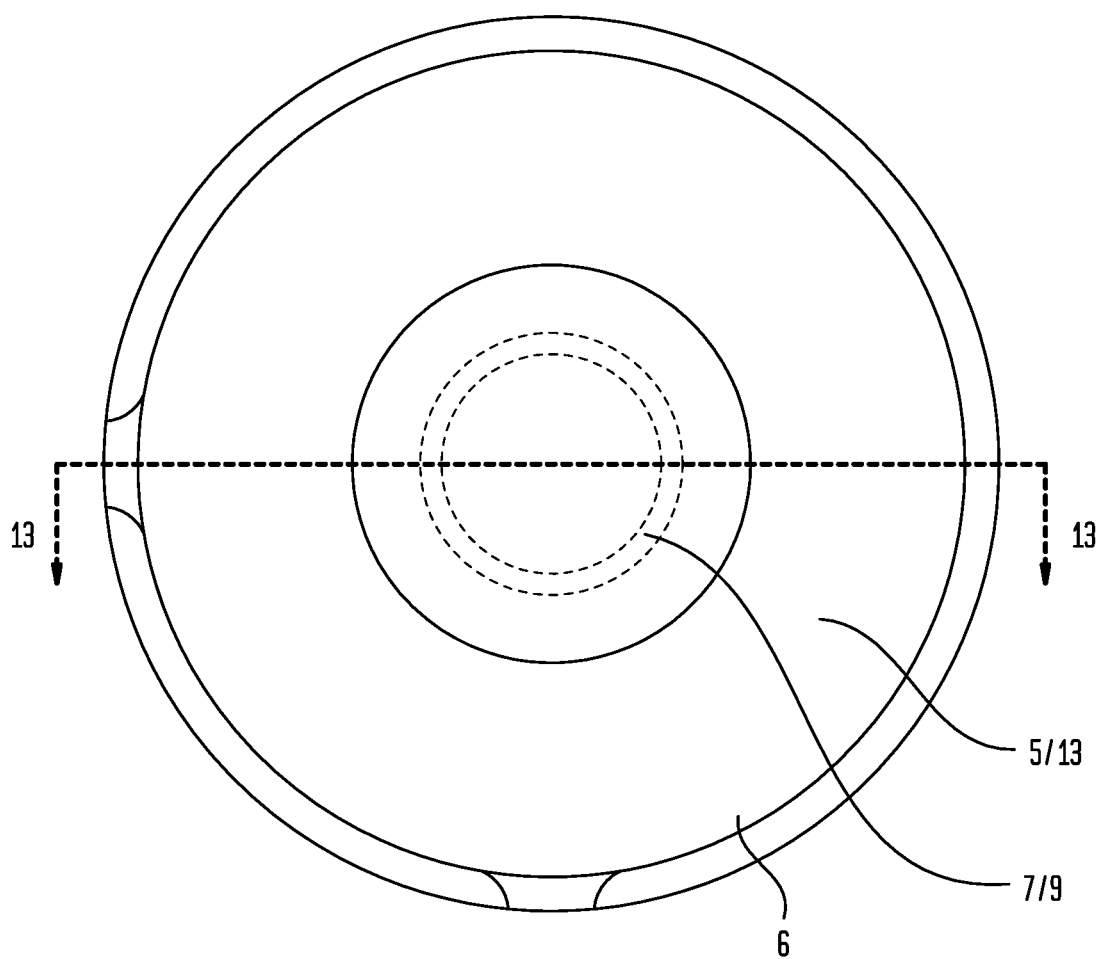
FIG. 12 is a front view of an embodiment of the flexible member including an electromagnet as a first magnetic force generator.
Figure 13:
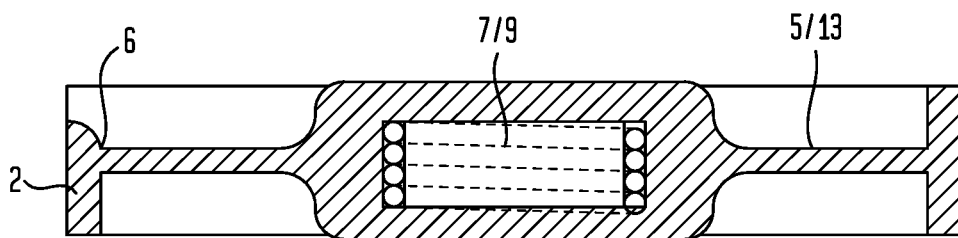
FIG. 13 is a cross section 13-13 of the flexible member shown in FIG. 12.
Figure 14:
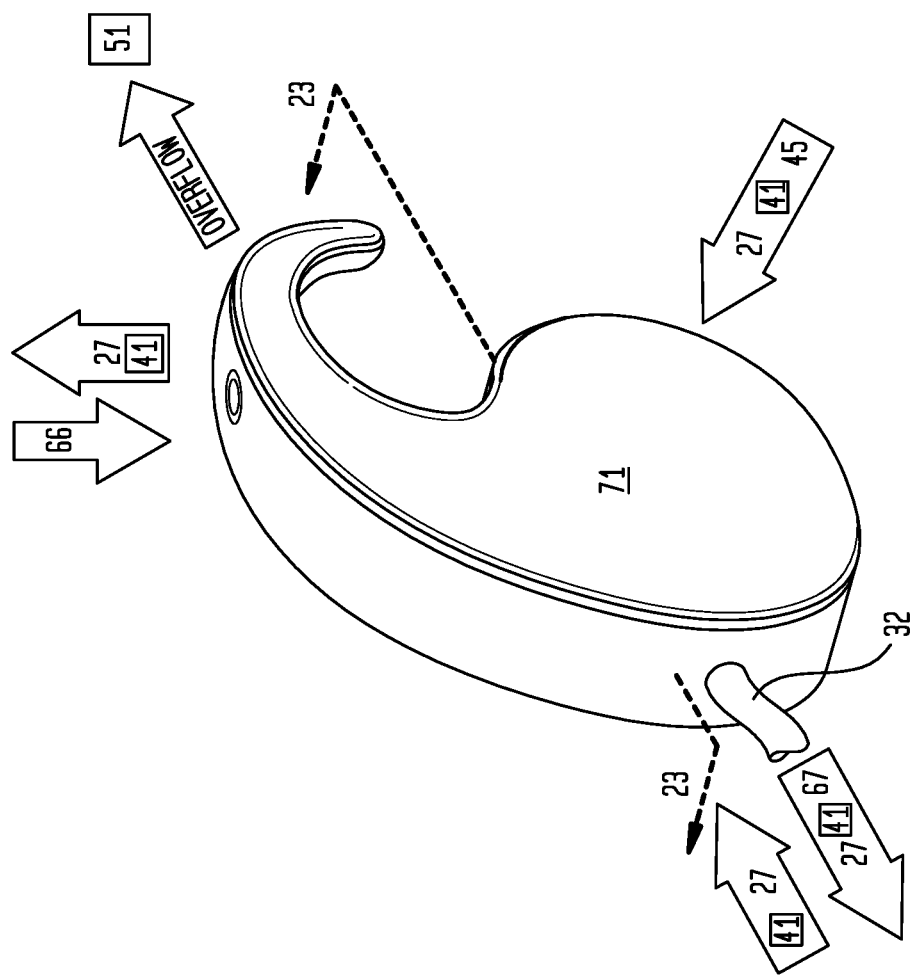
FIG. 14 is a perspective view of an embodiment of an external ear canal pressure regulation device including an embodiment of a magnetically driven pressure generator.
Figure 15:
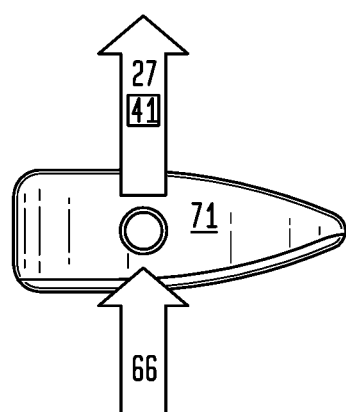
FIG. 15 is a top view of an embodiment of the external ear canal pressure regulation device including an embodiment of the magnetically driven pressure generator.
Figure 16:
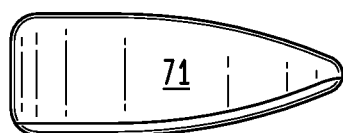
FIG. 16 is a bottom view of an embodiment of the external ear canal pressure regulation device including an embodiment of the magnetically driven pressure generator.
Figure 17:
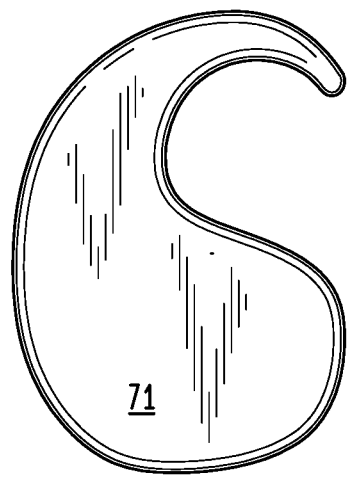
FIG. 17 is a first side view of an embodiment of the external ear canal pressure regulation device including an embodiment of the magnetically driven pressure generator.
Figure 18:
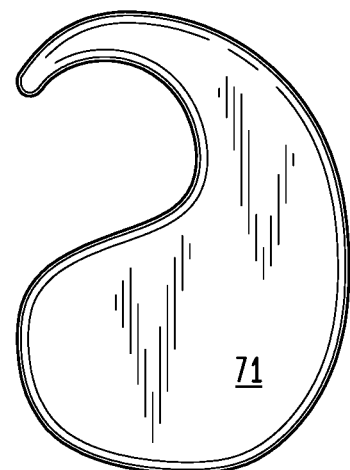
FIG. 18 is a second side view of an embodiment of the external ear canal pressure regulation device including an embodiment of the magnetically driven pressure generator.
Figure 19:
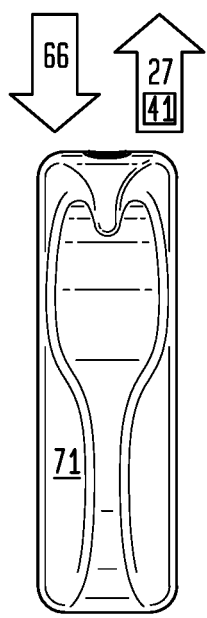
FIG. 19 is a front view of an embodiment of an embodiment of the external ear canal pressure regulation device including an embodiment of the magnetically driven pressure generator.
Figure 20:
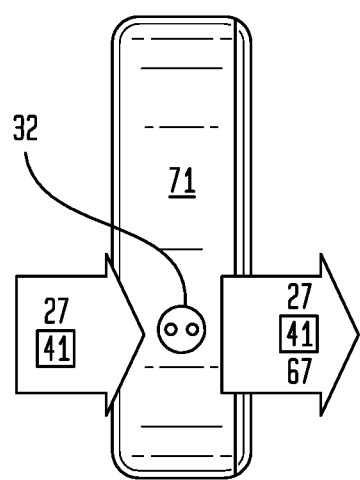
FIG. 20 is a back view of an embodiment of the external ear canal pressure regulation device including an embodiment of the magnetically driven pressure generator.
Figure 21:
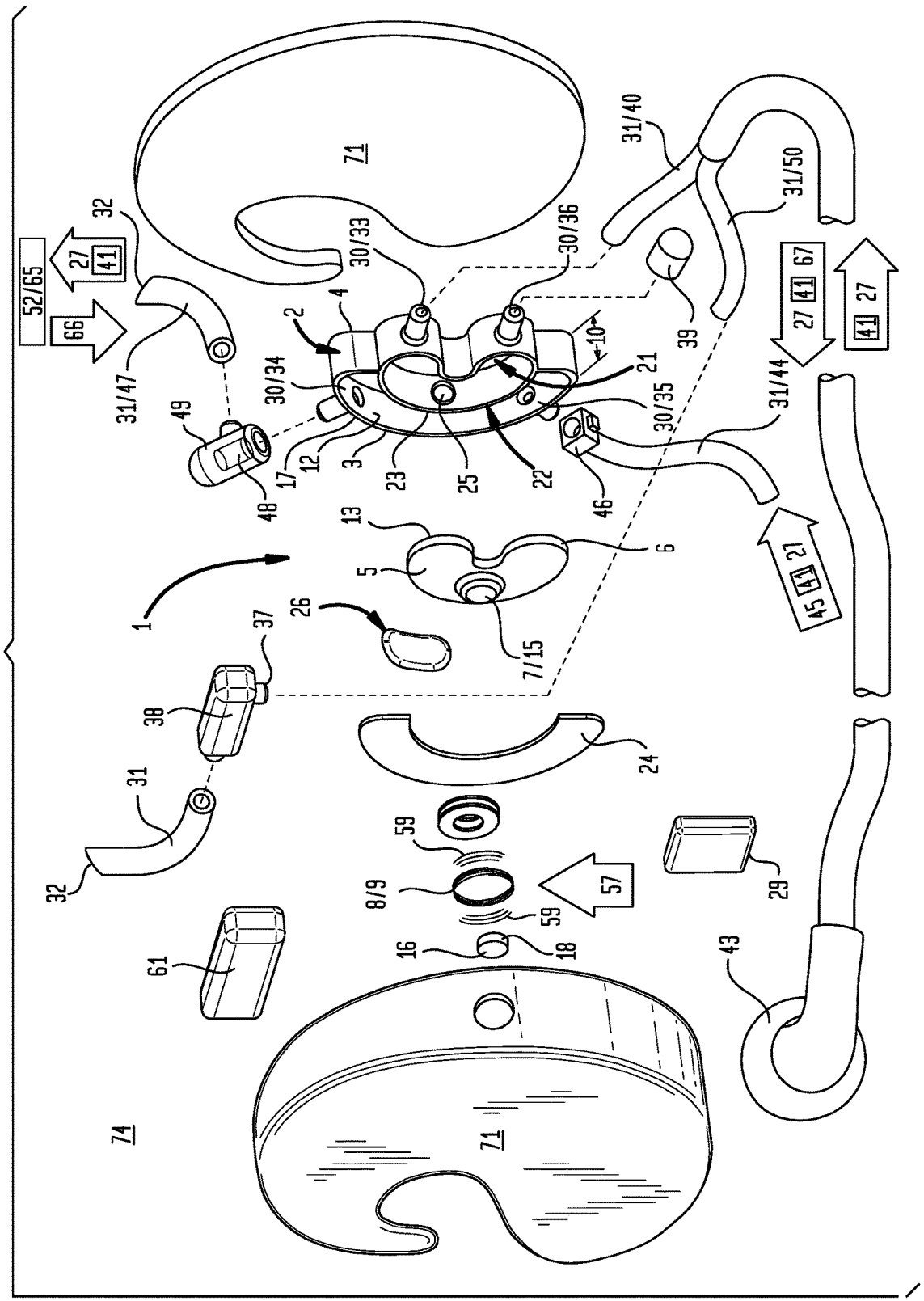
FIG. 21 is an exploded view of an embodiment of the external ear canal pressure regulation device including an embodiment of the magnetically driven pressure generator.
Figure 22:
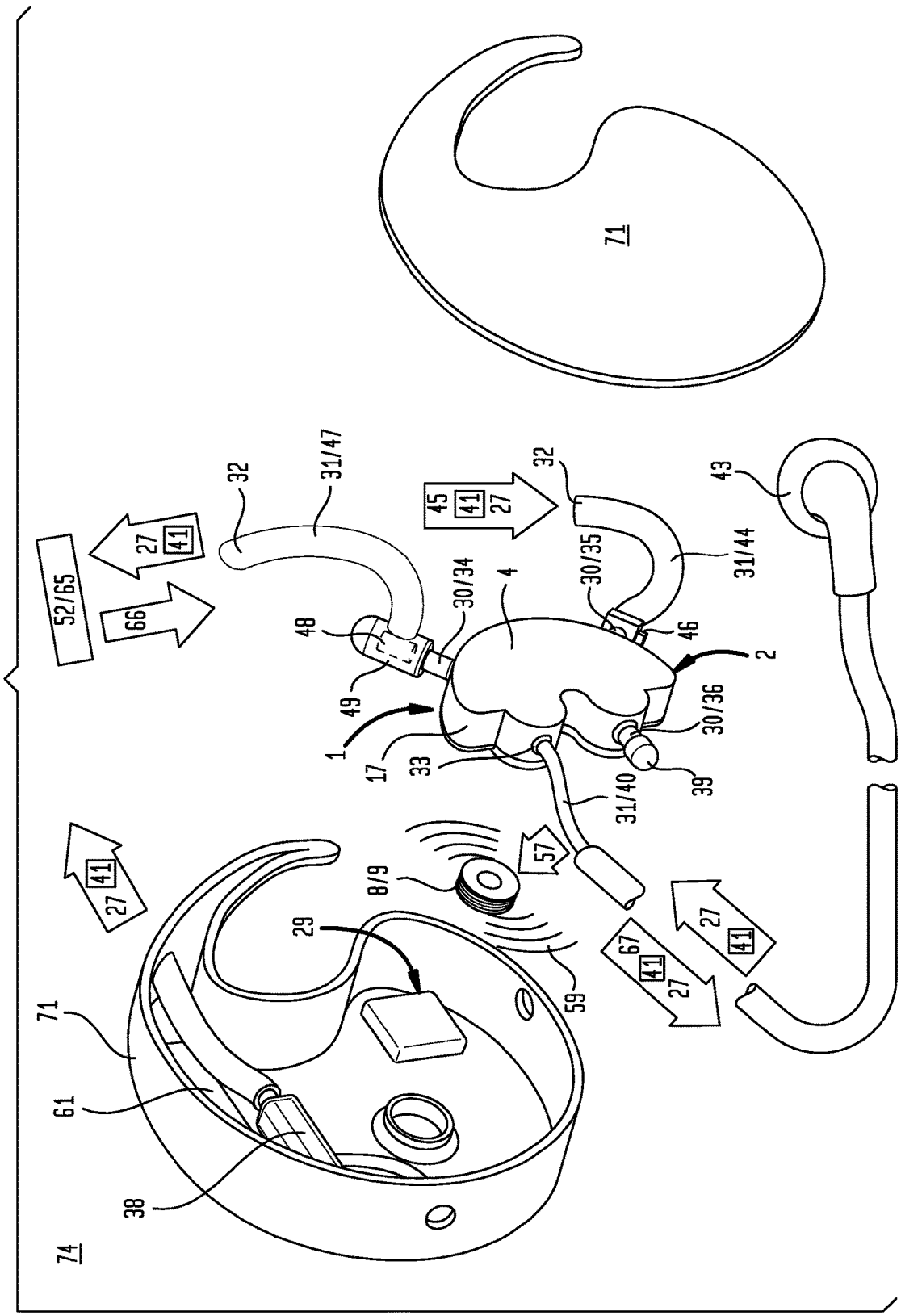
FIG. 22 is an exploded view of an embodiment of the external ear canal pressure regulation device including an embodiment of the magnetically driven pressure generator.
Figure 23:
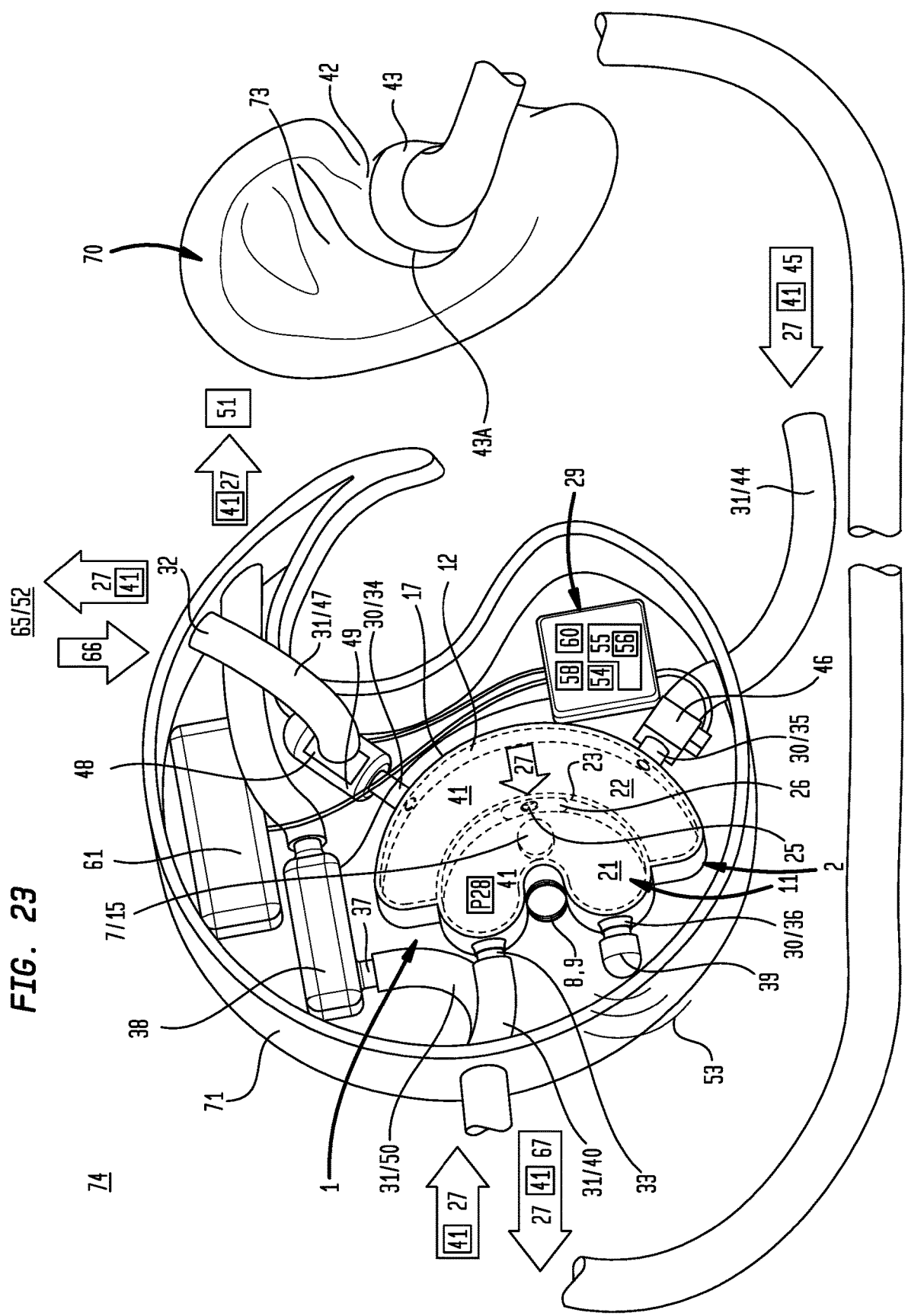
FIG. 23 is a first side view with the casing open to show the assembly of components of an embodiment of the external ear canal pressure regulation device including an embodiment of the magnetically driven pressure generator.
Figure 24:
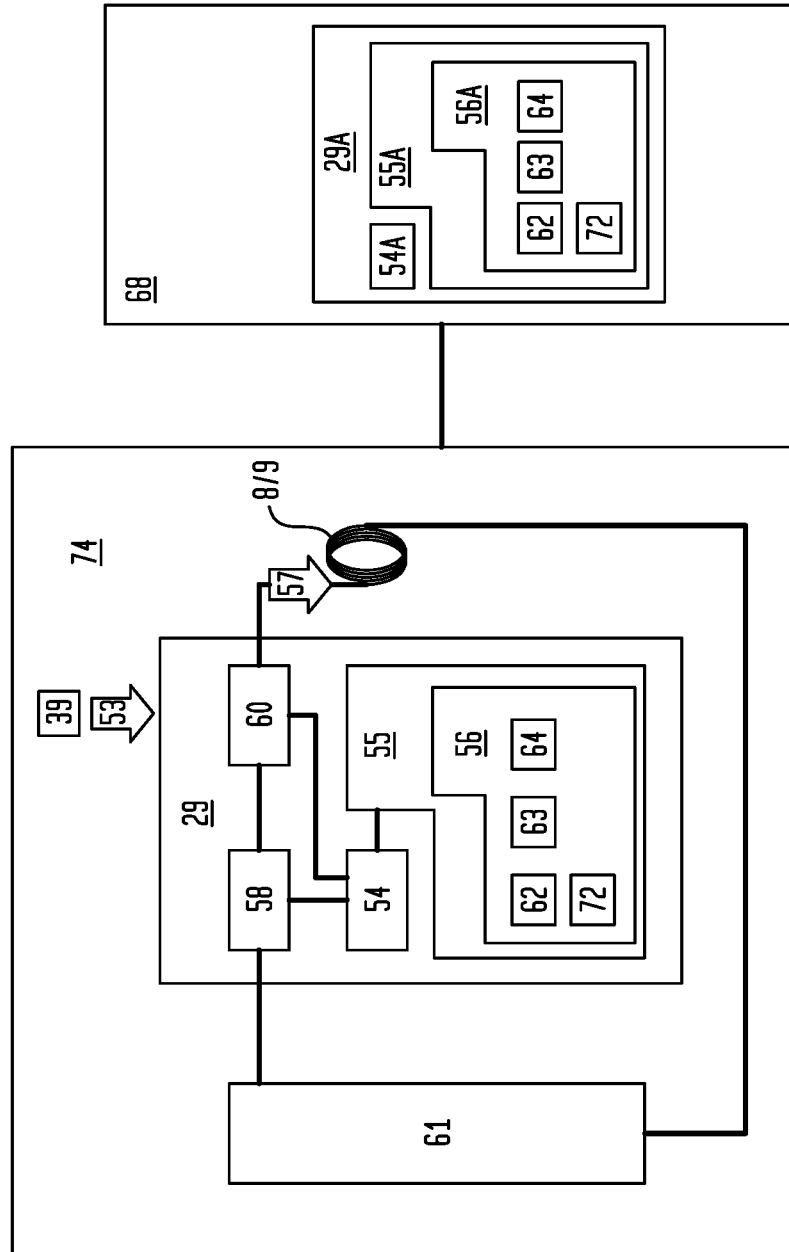
FIG. 24 is a schematic block diagram of a controller included in particular embodiments of the magnetically driven pressure generator or the external ear canal pressure regulation device.
Figure 25:
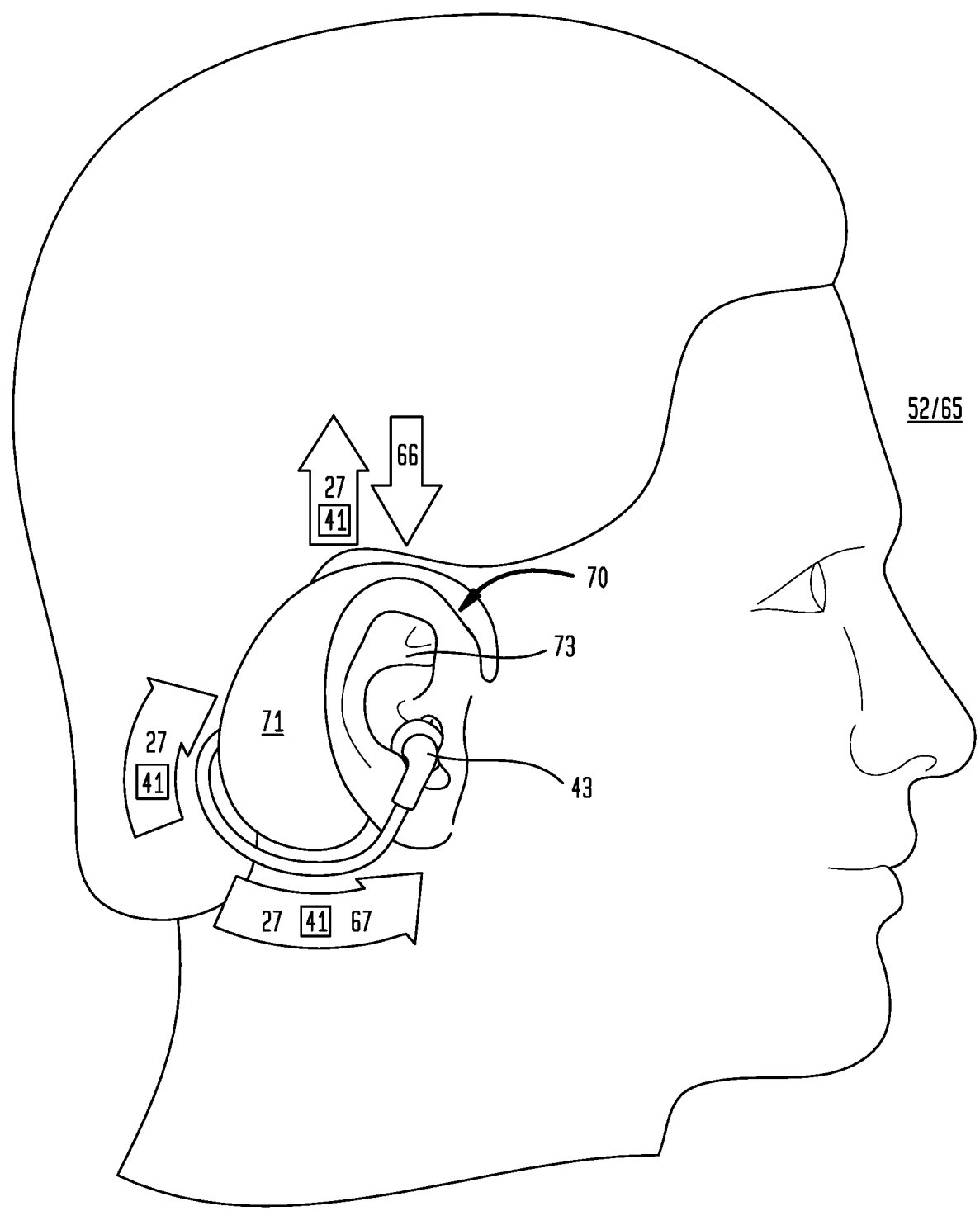
FIG. 25 is an illustration of a method of using an embodiment of the external ear canal pressure regulation device shown in FIGS. 14 through 24 including an embodiment of the magnetically driven pressure generator shown in FIGS. 1 through 24.

Now referring primarily to FIGS. 1 and 21, the housing (2) can have a housing depth (10) disposed between an open end (3) and a closed end (4). In particular embodiments, the housing (2) can be configured as a right cylinder (as shown in the illustrative example of FIGS. 1 through 5); however, this is not intended to preclude embodiments which otherwise include the housing (2) having a configuration in cross section, such as a rectangle, square, triangle, elliptical cylinder, or combinations thereof, or where the sides are arcuate or have an amount of curvature and are not linear. The housing (2) can be composed of a substantially non-electrically conducting, rigid material, such as plastic, rubber, elastomer, glass, ceramics, or the like. The housing (2) can be fabricated, molded, or formed from a plurality of pieces or as one-piece. As illustrative examples: sintering of metal powders, plastic injection molding, waterjet machining, or combinations thereof.

Now referring primarily to FIGS. 1 through 13, a flexible member (5) can be sealably engaged along the peripheral margin (6) proximate the open end (3) of the housing (2). The term "sealably engaged" means engagement of the peripheral margin (6) of the flexible member (5) at or proximate to the open end (3) of the housing (2) to effect a substantially fluid tight seal, and without limitation to the breadth of the foregoing, includes as illustrative examples, a substantially fluid tight seal effected by compression between surfaces of the peripheral margin (6) of the flexible member (5) at or proximate to the open end (3) of the housing (2), adhesive applied between the surfaces of the peripheral margin (6) of the flexible member (5) and the open end (3) of the housing (2), laser welding of the peripheral margin (6) of the flexible member (5) to the open end (3) of the housing (2), or combinations thereof. The flexible member (5) can comprise one or more of a substantially non-electrically conductive elastomer, thermoplastic, or other material that can flex or deform from a first position to a second position, resiliently or non-resiliently, to correspondingly increase or decrease the volume of the enclosed space (11) in the housing (2). Additionally, the flexible member (5) can be substantially fluid impermeable or partially fluid impermeable during the normal operating cycle of the magnetically driven pressure generator (1). The flexible member (5) can be disposed at or proximate the open end (3) of the housing (2) to define an enclosed space (11) inside the housing (2), the enclosed space (11) bound by the internal surface (12) of the housing (2) and a first side (13) of the flexible member (5).

Again, referring primarily to FIGS. 1 through 13, a first magnetic force generator (7) can be disposed on or in the flexible member (5), and a second magnetic force generator (8) can be disposed axially adjacent to the first magnetic force generator (7) and proximate to the closed end (4) or proximate the open end (3) of the housing (2), whether disposed in the enclosed space (11) or disposed external to the housing (2) (as shown in the illustrative example of FIGS. 1-5). As to particular embodiments, the first magnetic force generator (7) can be an electromagnetic force generator (9) and the second magnetic force generator (8) can be a magnet (15) (as shown in the illustrative example of FIG. 13), or the first magnetic force generator (7) can be a magnet (15) and the second magnetic force generator (8) can be an electromagnetic force generator (9) (as shown in the illustrative examples of FIGS. 1 through 11). The term "magnet" means a material that retains its magnetic properties in the absence of an inducing field or current and, without limitation to the breadth of the foregoing, can be a piece of metal surrounded by a magnetic field which can be aligned with, attracted to, or repelled by an external magnetic field, and as illustrative examples: neodynium iron boron, samarium cobalt, alnico, ceramic or ferrite, or the like. The term "electromagnetic force generator" means an electrically conductive winding of a conductive material which upon passage of an electrical current generates a magnetic field (59) and, without limitation to the breadth of the foregoing, can as illustrative examples be one or more electrically conductive windings of: copper, silver, brass, or other like conductive materials or combinations thereof.

Again, referring primarily to FIGS. 1 through 5, particular embodiments can, but need not necessarily, include a first ferromagnetic core (16). The term "ferromagnetic core" means a body susceptible to magnetization in an applied electromagnetic field and, without limitation to the breadth of the foregoing, can be a one-piece body or a body comprising a plurality of layers of material susceptible to magnetization, such as: nickel, iron, cobalt, or other like material, or combinations thereof. In particular embodiments, the first magnetic force generator (7) coupled to the flexible member (5) can be a magnet (15) and the second magnetic force generator (8) can be an electromagnetic force generator (9) with the first ferromagnetic core (16) having a location responsive to the second magnetic force generator (8). In particular embodiments, the first ferromagnetic core (16) can be generally axially aligned with the first magnetic force generator (7). As to particular embodiments, the electromagnetic force generator (9) can engage the first ferromagnetic core (16) or be disposed a spaced distance about the first ferromagnetic core (16). As to particular embodiments, the second magnetic force generator (8) can comprise a plurality of metal windings wound about the external surface (17) of the housing (2) proximate to the closed end (4), and the first ferromagnetic core (16) can be disposed a spaced distance apart within the electromagnetic force generator (9) axially aligned with the first magnetic force generator (7) (as shown in the illustrative example of FIG. 5). In particular embodiments, the second magnetic force generator (8) can comprise a plurality of windings wound about the ferromagnetic core external surface (18) with the first ferromagnetic core (16) substantially axially aligned with the first magnetic force generator (7).

Now referring primarily to FIGS. 1 through 5, particular embodiments can, but need not necessarily, include a third magnetic force generator (19), which can be disposed at or proximate to the open end (3) or the closed end (4) of the housing (2). The third magnetic force generator (19) can be a magnet (15) or electromagnetic force generator (9), as described above. As to embodiments that include a third magnetic force generator (19) in the form of an electromagnetic force generator=(9), a second ferromagnetic core (20) can, but need not necessarily, be disposed proximate to the open end (3) of the housing (2) at a location to which the second ferromagnetic core (20) can be responsive to the electromagnetic field applied by the electromagnetic force generator (9). The second ferromagnetic core (20) can be disposed to generally axially align with the first magnetic force generator (7) disposed on the flexible member (5).

Now referring primarily to FIGS. 14 through 23, in particular embodiments, the housing (2) can, but need not necessarily, be partitioned into a first fluid chamber (21) and a second fluid chamber (22) by a partition wall (23). The partition wall (23) can be sealably engaged with the closed end (4) of the housing (2) and extend to the open end (3) of the housing (2). The flexible member (5) can be sealably engaged along the peripheral margin (6) at or proximate to the open end (3) of the first fluid chamber (21). A cover (24) can be sealably engaged to or proximate the open end (3) of the second fluid chamber (22). The cover (24) can be comprised of one or more substantially non-electrically conductive elastomers, thermoplastics, or the like. Additionally, the cover (24) can be substantially fluid impermeable during the normal operating cycle of the magnetically driven pressure generator (1). The partition wall (23) can further include an aperture (25) communicating between the first fluid chamber (21) and second fluid chamber (22). A first unidirectional valve (26) can be disposed in the partition wall (23) to permit a fluid flow (27) to move in only one direction between the first and second chambers (21)(22). The first unidirectional valve (26) disposed in the partition wall (23) can be responsive to negative or positive fluid pressure (28) within the first or second fluid chambers (21)(22) (as shown in the illustrative example of FIGS. 21 and 23, the first unidirectional valve (26) can comprise a flap valve) or the first unidirectional valve (26) can be an electrically operable between an open condition and a closed condition in response to a signal from a controller (29), as further described below.

Again, referring primarily to FIGS. 1 through 23, particular embodiments can, but need not necessarily, further include one or more ports (30) disposed in the housing (2) which communicate between the internal surface (12) and external surface (17) of the housing (2). Particular embodiments can, but need not necessarily, further include conduits (31) engaged to the one or more ports (30) to extend the enclosed space (11) of the housing (2) to the distal end (32) of the conduits (31) allowing an increase or decrease of fluid pressure (28) or fluid flow (27) within the conduits (31) at the distal end (23). As to particular embodiments, the housing (2) can include one or more of a fluid outlet port (33), a fluid bleed port (34), a fluid inlet port (35), and a pressure sensor port (36). The fluid outlet port (33) can communicate between the external surface (17) and the internal surface (12) of the housing (2) to provide a fluid flow (27) from the enclosed space (11) (as to the illustrative embodiments of FIGS. 1-13) or from the first fluid chamber (21) (as shown in the illustrative embodiments of FIGS. 14-23). A fluid delivery conduit (40) can be sealably engaged to the fluid outlet port (33) for delivery of an amount of fluid (41) to the distal end (32) of the fluid delivery conduit (40), which can, but need not necessarily, be disposed to deliver an amount of fluid (41) from the enclosed space (11) of the housing (2) or the first chamber (21).

Now referring primarily to FIGS. 14-23, a fluid inlet port (35) can communicate between the external surface (17) and the internal surface (12) of the housing (2) of the second chamber (22). The fluid inlet port (35) can sealably engage a fluid inlet conduit (44) open to atmosphere in the ambient environment (65) or coupled to a fluid source (45) which can contain an amount of fluid (41). The amount of fluid (41) contained by the fluid source (45) can be, as illustrative examples: a liquid, a gel, a viscous polymer, or other material, or combinations thereof, which deforms continuously for delivery from the fluid source (45) into the second fluid chamber (22). The amount of fluid (41) contained in the fluid source (45) can be delivered as a fluid flow (27) from the fluid source (45) under force of one or more of: gravity, pressurized head space, a fluid pump, or combinations thereof. As to particular embodiments, a fluid inlet valve (46) can be disposed between the fluid inlet port (35) and the fluid source (45) to intermittently or continuously interrupt flow of an amount of fluid (41) to or from the second fluid chamber (22) toward the fluid source (45).

Again, referring primarily to FIGS. 14 through 23, the fluid bleed port (34) can communicate between the external surface (17) and internal surface (12) of the housing (2) of the second chamber (22). The fluid bleed port (34) can sealably engage a fluid bleed conduit (47) and the distal end (32) of the fluid bleed conduit (47) can be disposed in the ambient environment (65). The fluid bleed conduit (43) can conduct an amount of fluid (41) from the second chamber (22) to the ambient environment (65). If the amount of fluid (41) delivered from the fluid source (45) exceeds the volume of the second fluid chamber (22), the excess amount of fluid (38) can egress from the second fluid chamber (22) through the fluid bleed port (34) and the fluid bleed conduit (47) to the ambient environment (65).

Again, referring primarily to FIGS. 14 through 23, as to particular embodiments, a fluid flow generator (49) can be coupled between the fluid bleed port (35) and the distal end (32) of the fluid bleed conduit (46). The fluid flow generator (49) can operate in the first instance to provide the bleed valve (48) in the open condition, which allows egress of an excess amount of fluid (41) from the second fluid chamber (22). The fluid flow generator (49) in the second instance can operate to generate a flow of air (66) from the ambient environment (65) into the second fluid chamber (22) to move the amount of fluid (41) contained in the second fluid chamber (22) through the aperture (25) disposed in the partition wall (23) into the first fluid chamber (21).

Now referring primarily to FIGS. 1 through 23, embodiments can, but need not necessarily, further include a fluid pressure relief valve (38). As to particular embodiments, the fluid pressure relief valve (38) can be coupled to a pressure relief port (37) which communicates between the external surface (17) and the internal surface (12) of the housing (2) of the enclosed space (11) (as shown in the illustrative example of FIGS. 1 through 5). As to other embodiments, a fluid return conduit (50) can, but need not necessarily, be fluidicly coupled to the fluid delivery conduit (40) to return the amount of fluid (41) to the fluid source (45), a fluid collection vessel (51), or discharge the amount of fluid to the ambient environment (65) (as shown in the illustrative examples of FIGS. 14 through 23). As to these embodiments the pressure relief valve (38) can operate between a closed condition to generate an amount of fluid pressure (28) in the first fluid chamber (21), the fluid delivery conduit (40), or the fluid return conduit (50), and an open condition to relieve an amount of fluid pressure (28) in the first fluid chamber (21), the fluid delivery conduit (40), or the fluid return conduit (50).

As illustrative examples, the pressure release valve (38) can be configured to relieve an amount of pressure (28) in the enclosed space (11) or first fluid chamber (21) when the amount of pressure (28) exceeds a pre-selected pressure (28) to actuate the pressure release valve (38). In one illustrative embodiment, the pressure release valve (38) can be disposed in the open condition when the amount of pressure (28) exceeds 5.0 psi (pounds per square inch; about 34 kPa; 1 psi=about 6.8 kPa). As to particular embodiments, the pressure release valve (38) can be disposed in the open condition in response to lesser or greater amounts of pressure (28) in a range of about 0 psi to 20 psi (about 0 kPa to about 137.8 kPa). The amount of pressure (28) can be selected from the group including or consisting of: about 0.0 psi to about 1.0 psi, about 0.5 psi to about 1.5 psi, about 1.0 psi to about 2.0 psi, about 1.5 psi to about 2.5 psi, about 2.0 psi to about 3.0 psi, about 2.5 psi to about 3.5 psi, about 3.0 psi to about 4.0 psi, about 3.5 psi to about 4.5 psi, about 4.0 psi to about 5.0 psi, about 4.5 psi to about 5.5 psi, about 5.0 psi to about 6.0 psi, about 5.5 psi to about 6.5 psi, about 6.0 psi to about 7.0 psi, about 6.5 psi to about 7.5 psi, about 7.0 psi to about 8.0 psi, about 7.5 psi to about 8.5 psi, about 8.0 psi to about 9.0 psi, about 8.5 psi to about 9.5 psi, about 9.0 psi to about 10.0 psi, about 9.5 psi to about 10.5 psi, about 10.0 psi to about 11.0 psi, about 10.5 psi to about 11.5 psi, about 11.0 psi to about 12.0 psi, about 11.5 psi to about 12.5 psi, about 12.0 psi to about 13.0 psi, about 12.5 psi to about 13.5 psi, about 13.0 psi to about 14.0 psi, about 13.5 psi to about 14.5 psi, about 14.0 psi to about 15.0 psi, about 14.5 psi to about 15.5 psi, about 15.0 psi to about 16.0 psi, about 15.5 psi to about 16.5 psi, about 16.0 psi to about 17.0 psi, about 16.5 psi to about 17.5 psi, about 17.0 psi to about 18.0 psi, about 17.5 psi to about 18.5 psi, about 18.0 psi to about 19.0 psi, about 18.5 psi to about 19.5 psi, and about 19.0 psi to about 20.0 psi.

The foregoing embodiments are not intended to preclude embodiments which dispose the pressure release valve (24) in the open condition at a fluid pressure (28) of greater than 20 psi, depending on the application.

Now referring primarily to FIGS. 1 through 23, particular embodiments can, but need not necessarily, further include a pressure sensor (39). The pressure sensor (39) can be fluidicly coupled to the enclosed space (11) of the housing (2) or first fluid chamber (21) to sense the amount of pressure (28) inside the enclosed space (11) or first fluid chamber (21). The pressure sensor (39) can generate a signal (53) which varies based on the increase or decrease of pressure (28) within the enclosed space (11) or first fluid chamber (21) within the housing (2).

Now referring generally to FIGS. 1 through 24, with particular reference to FIGS. 21 through 24, particular embodiments can, but need not necessarily, further include a controller (29) including a controller processor (54) communicatively coupled to a controller non-transitory computer readable media (55) containing a computer program (56) executable by the controller processor (54) to control the direction and magnitude of current (57) in the one or more electromagnetic force generators (9). The controller (29) can be contained inside of the magnetically driven pressure generator (1) or within a casing (71) enclosing the magnetically driven pressure generator (1) or can be electronically coupled (whether wired or wirelessly) through intermediary hardware to an external controller (29A) in which the processor (54A) the non-transitory computer readable medium (55A) containing the computer program (56A) resides in a mobile device (68), such as: a cellular telephone, tablet computer, laptop computer, or other computer implemented device in which the computer program (56A) can reside.

As to particular embodiments, the computer program (56)(56A) can operate a current controller (58) electrically coupled to one or more electromagnetic force generators (9)(19). The current controller (58) can function to control the magnitude of the current (57) conducted through the one or more electromagnetic force generators (9)(19). The current controller (58) can be adapted for use with alternating current, direct current, or both. The magnetic field (59) generated by the electromagnetic force generator (9) can be proportional to the magnitude of the current (57). Accordingly, the current controller (58), by varying the amplitude of the current (57), can correspondingly continuously or intermittently vary the strength of the magnetic field (59) to correspondingly continuously control flexure of the flexible member (5) to intermittently or continuously precisely form pressure waves (67) having pre-selected amplitude and frequency values (63)(64) over time.

As to particular embodiments, the computer program (56) can further operate a polarity controller (60) electrically coupled to the one or more electromagnetic force generators (9). The polarity controller (60) operates to control the direction of the current (57) being conducted through the one or more electromagnetic force generators (9)(19). The direction of magnetic polarity generated by the electromagnetic force generator (9) can be changed by correspondingly changing the direction of current (57) flowing in the electromagnetic force generator (9)(19). Accordingly, the polarity controller (60) can, by changing the direction of the current (57) in the electromagnetic force generator, (9)(19) correspondingly change the direction of the magnetic polarity generated by the electromagnetic force generator (9)(19).

Particular embodiments can further include a power source (61). The power source (61) can be electrically coupled to the one or more electromagnetic force generators (9) directly, through intermediary hardware (the microprocessor, a current controller, a polarity controller), or both. Further, the power source (61) can provide power convertible to alternating current, direct current, or both.

Now referring primarily to FIGS. 1 through 23, particular embodiments of the magnetically driven pressure generator (1) can be used to generate either an increase or decrease in pressure (28) of a fluid flow (27) of an amount of fluid (41) in or from the enclosed space (11) or the first fluid chamber (21) depending on the embodiment. As an illustrative example, referring to FIGS. 1 through 13, the magnetically induced pressure generator (1) can be configured to operate the second magnetic force generator (8) to induce an amount of flexure in the flexible member (5) to correspondingly alter the volume of the enclosed space (11) to correspondingly increase or decrease pressure of an amount of fluid (41) contained therein. A gas contained in a closed system, exhibits an inverse relationship between pressure and volume. Accordingly, if the flexible member (5) flexes toward the closed end (4) of the housing (2), the volume of the enclosed space (11) correspondingly decreases, and the fluid pressure (28) of the gas within the enclosed space (11) can correspondingly increase. Conversely, if the flexible member (5) flexes away from the closed end (4) of the housing (2), the volume of the enclosed space (11) correspondingly increases, and the pressure of the gas within the enclosed space (11) correspondingly decreases. In the aforementioned particular embodiments, the amplitude of change in pressure (28) of the gas in the enclosed space (11) can be proportionate to the amount of flexure of the flexible member (5) induced by attracting or repulsing forces generated between the first magnetic force generator (7) and the second magnetic force generator (8). Additionally, alternating the attracting and repulsing forces generated between the first magnetic force generator (7) and the second magnetic force generator (8) can correspondingly generate oscillation in the flexible member (5) in an oscillation period independent of the oscillation amplitude. Accordingly, pressure waves can be precisely generated in the enclosed space (11) of the housing (2) having a pre-selected amplitude or frequency values (63)(64) over a period of time by operation of the current controller (58) and the polarity controller (60).

Referring primarily to FIGS. 14 through 23, particular embodiments of the magnetically driven pressure generator (1) can operate to alter fluid pressure (28) or generate a fluid flow (27) in an amount of fluid (41), whether the fluid is a liquid or a gas. As an illustrative example, the enclosed space (11) can, as above described, include a first fluid chamber (21), a second chamber (22), a fluid delivery conduit (40), a fluid return conduit (50), and an earpiece (43) coupled to the fluid delivery conduit (40) and the fluid return conduit (50) which can be disposed in or sealably engaged to the external ear canal (42). The fluid inlet valve (46) can be disposed in the open condition to allow an amount of fluid (41) to be delivered from the fluid source (45) through the fluid inlet conduit (44) to the second fluid chamber (22). As an amount of fluid (41) flows into the second fluid chamber (22), the bleed valve (48) within the fluid flow generator (49) can be disposed in the open condition to permit air inside the second fluid chamber (22) to flow through the fluid bleed conduit (47) and to the ambient environment (65). Once the second fluid chamber (22) contains an amount of fluid (22), the fluid flow generator (49) can be further operated to generate a flow of air (67) into the second fluid chamber (22) to force the amount of fluid (41) within the second fluid chamber (22) through the aperture (25) disposed in the partition wall (23) into the first fluid chamber (21). The first unidirectional valve (26) operates to prohibit fluid flow (27) from the first fluid chamber (21) back into the second fluid chamber (22). By operation of the flexible member (5) the amount of fluid (41) can then be delivered from the first fluid chamber (21) through the fluid delivery conduit (40) and through the fluid return conduit (50). As one illustrative example, the fluid delivery conduit (40) and the fluid return conduit (50) can be disposed in the external ear canal (42) of an ear (70), and as to certain embodiments, the fluid delivery conduit (40) and the fluid return conduit (50) can pass through or be surrounded by an earpiece (43) which can be disposed in or sealably engaged with the external ear canal (42) of the ear (70). The amount of fluid (41) can be delivered into the external ear canal (42) from the fluid delivery conduit (40), circulate in the external ear canal (42), pass into the fluid return conduit (50), and through the pressure release valve (38) in the open condition. The pressure relief valve (38) can then be disposed in the closed condition to allow the pre-selected fluid pressure (28) to be generated in the fluid delivery conduit (40), the fluid return conduit (50), and in the external ear canal (42) of the ear (70) when the earpiece (43) engages or sealably engages the external ear canal (42).

As above described, operation of the first magnetic force generator (7) and the second magnetic force generator (8) can effect an amount of flexure in the flexible member (5) to correspondingly alter the volume of the first fluid chamber (21) to correspondingly increase or decrease fluid pressure of the fluid (41) therein. The flexure of the flexible member (5) toward the closed end (4) of the housing (2) can decrease the volume of the first fluid chamber (21), without substantially increasing or decreasing the surface area of the first fluid chamber (21) or volume of amount of fluid (38) within the first fluid chamber (21), thereby increasing the fluid pressure (28) within the first fluid chamber (21). The flexure of the flexible member (5) can also occur away from the closed end (4) of the housing (2), which increases the volume of the first fluid chamber (21) without substantially increasing or decreasing the surface area of the first fluid chamber (21) or volume of amount of fluid (41) within the first fluid chamber (21), thereby decreasing the fluid pressure (28) within the first fluid chamber (21). In the aforementioned particular embodiments, the amplitude of change in fluid pressure (28) of the amount of fluid (41) in the first fluid chamber (21) can be proportionate to the amount of flexure of the flexible member (5) induced by attracting or repulsing forces generated between the first magnetic force generator (7) and the second magnetic force generator (8). Additionally, alternating the attracting and repulsing forces generated between the first magnetic force generator (7) and the second magnetic force generator (8) can correspondingly generate oscillation in the flexible member (5) in an oscillation period independent of the oscillation amplitude. Accordingly, pressure waves (67) can be generated in the first fluid chamber (21) having a pre-selected amplitude (63) and frequency values (64) by operation of the current controller (58) and the polarity controller (60).

Again, referring to FIG. 5, in particular embodiments, a third magnetic force generator (19) can be included comprising either a magnet (15) or electromagnetic force generator (9) to further interact with the attracting forces or repulsing forces of the first magnetic force generator (7) and second magnetic force generator (8), flexing the flexible member (5) accordingly, as described above.

In a particular embodiment, the operation of the program (56) can be executed to oscillate the flexible member (5) as described above, at a pre-selected oscillation frequency (64). The oscillation frequency (64) can be in a range of about 0 to about 100 kiloHertz (kHz). The oscillation frequency can be selected from the group including or consisting of: about 0 kHz to about 5.0 kHz, about 2.5 kHz to about 7.5 kHz, about 5.0 kHz to about 10.0 kHz, about 7.5 kHz to about 12.5 kHz, about 10.0 kHz to about 15.0 kHz, about 12.5 kHz to about 17.5 kHz, about 15.0 kHz to about 20.0 kHz, about 17.5 kHz to about 22.5 kHz, about 20.0 kHz to about 25.0 kHz, about 22.5 kHz to about 27.5 kHz, about 25.0 kHz to about 30.0 kHz, about 27.5 kHz to about 32.5 kHz, about 30.0 kHz to about 35.0 kHz, about 32.5 kHz to about 37.5 kHz, about 35.0 kHz to about 40.0 kHz, about 37.5 kHz to about 42.5 kHz, about 40.0 kHz to about 45.0 kHz, about 42.5 kHz to about 47.5 kHz, about 45.0 kHz to about 50.0 kHz, about 47.5 kHz to about 52.2 kHz, about 50.0 kHz to about 55.0 kHz, about 52.5 kHz to about 57.5 kHz, about 55.0 kHz to about 60.0 kHz, about 57.5 kHz to about 62.5 kHz, about 60.0 kHz to about 65.0 kHz, about 62.5 kHz to about 67.5 kHz, about 65.0 kHz to about 70.0 kHz, about 67.5 kHz to about 72.5 kHz, about 70.0 kHz to about 75.0 kHz, about 72.5 kHz to about 77.5 kHz, about 75.0 kHz to about 80.0 kHz, about 77.5 kHz to about 82.5 kHz, about 80.0 kHz to about 85.0 kHz, about 82.5 kHz to about 87.5 kHz, about 85.0 kHz to about 90.0 kHz, about 87.5 kHz to about 92.5 kHz, about 90.0 kHz to about 95.0 kHz, about 92.5 kHz to about 97.5 kHz, about 95.0 kHz to about 100 kHz, and combinations thereof.

In yet another particular embodiment, the computer program (56) can be executed to generate a pre-selected pressure amplitude (63), whether a positive pressure or negative pressure as compared to the ambient pressure (52) in the enclosed space (11) or first fluid chamber (21), depending upon the embodiment and application. In one illustrative embodiment, the range of pre-selected pressure amplitude (63) can be about 0 psi to about 5 psi (about 0 kPa to about 34.4 kPa; 1 psi=6.8 kPa). In another illustrative embodiment, the pre-selected pressure amplitude (63) can be a range of pressures of about 0 psi to about 20 psi (about 0 kPa to about 137.8 kPa; 1 psi=6.8 kPa). The pre-selected pressure amplitude (63) in the closed space (11) or the first fluid pressure chamber (21) can be selected from the group including or consisting of: about 0.0 psi to about 1.0 psi, about 0.5 psi to about 1.5 psi, about 1.0 psi to about 2.0 psi, about 1.5 psi to about 2.5 psi, about 2.0 psi to about 3.0 psi, about 2.5 psi to about 3.5 psi, about 3.0 psi to about 4.0 psi, about 3.5 psi to about 4.5 psi, about 4.0 psi to about 5.0 psi, about 4.5 psi to about 5.5 psi, about 5.0 psi to about 6.0 psi, about 5.5 psi to about 6.5 psi, about 6.0 psi to about 7.0 psi, about 6.5 psi to about 7.5 psi, about 7.0 psi to about 8.0 psi, about 7.5 psi to about 8.5 psi, about 8.0 psi to about 9.0 psi, about 8.5 psi to about 9.5 psi, about 9.0 psi to about 10.0 psi, about 9.5 psi to about 10.5 psi, about 10.0 psi to about 11.0 psi, about 10.5 psi to about 11.5 psi, about 11.0 psi to about 12.0 psi, about 11.5 psi to about 12.5 psi, about 12.0 psi to about 13.0 psi, about 12.5 psi to about 13.5 psi, about 13.0 psi to about 14.0 psi, about 13.5 psi to about 14.5 psi, about 14.0 psi to about 15.0 psi, about 14.5 psi to about 15.5 psi, about 15.0 psi to about 16.0 psi, about 15.5 psi to about 16.5 psi, about 16.0 psi to about 17.0 psi, about 16.5 psi to about 17.5 psi, about 17.0 psi to about 18.0 psi, about 17.5 psi to about 18.5 psi, about 18.0 psi to about 19.0 psi, about 18.5 psi to about 19.5 psi, about 19.0 psi to about 20.0 psi, and combinations thereof. The above embodiments are illustrative only, as the pre-selected pressure amplitude can be selected from the range of about 0 psi to about any pre-selected pressure amplitude, depending on the application.

By combining pre-selected pressure amplitudes (63) in various combinations and permutations with pre-selected oscillation frequencies (64) over a period of time, stable pressure amplitudes (63) (whether positive or negative relative to the ambient pressure (52)) or pressure waves (67) having preselected amplitude values (63) or frequency values (64), or combinations thereof, can be generated in the enclosed space (11) or the first fluid pressure chamber (21) to track pre-selected pressure profiles (62) of the program (56). To ensure that the pre-selected amplitude and frequency values (63)(64) or pre-selected pressure profiles (62) are achieved, the pressure sensor signal (53) generated by the pressure sensor (39) coupled to the pressure sensor port (36) can be analyzed by a feedback module (72) of the computer program (56) to correspondingly alter operation of the flexible member (5).

Now referring primarily to FIGS. 21 through 25, as to particular embodiments, the distal ends (32) of the fluid delivery conduit (40) or the fluid return conduit (50) can be disposed in the external ear canal (42) of an ear (70). An amount of fluid (41) can be delivered from the first fluid chamber (21) of the housing (2) to the distal end (32) of the fluid delivery conduit (40) into the external ear canal (42) of an ear (70) and egress the external ear canal (42) of the ear (70) through the fluid return conduit (50). The pressure relief valve (38) can be disposed in the open condition or closed condition depending on the amount of fluid pressure (28) to be generated in the external ear canal (42) of the ear (70). As to particular embodiments, the pressure relief valve (38) can be maintained in the open condition to allow an amount of fluid (41) to circulate in the external ear canal (42) of the ear (70) at a relatively low fluid pressure (28). As to other embodiments, the pressure relief valve (38) can be maintained in the closed condition or intermittently closed condition to generate a continuous or substantially continuous fluid pressure (28) (whether negative or positive compared to ambient pressure (52)) or a variable fluid pressure (28), or a fluid pressure adjusted over a period time to track a pre-selected pressure profile (62) (a set of pre-selected pressure values over a period of time).

Again referring primarily to FIGS. 14 through 25, embodiments can further include a casing (71) which encloses or operably supports one or more of: the housing (2), the magnetic force generators (8)(9)(19), ferromagnetic cores (16)(20), fluid flow generator (49), controller (29), conduits (31), and associated circuitry. The casing (71), as to particular embodiments, can be configured to couple, connect, attach, or bring embodiments of the magnetically driven pressure generator (1) into proximity with an object or person for use. As shown in the illustrative example of FIG. 25, the casing (71) can be configured to provide an external ear canal pressure regulation device (74) which can be disposed behind and about the auricle (73) of the ear (70).

As can be easily understood from the foregoing, the basic concepts of the present invention may be embodied in a variety of ways. The invention involves numerous and varied embodiments of a magnetically driven pressure generator and methods for making and using such a magnetically driven pressure generator including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus team or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "electromagnetic force generator" should be understood to encompass disclosure of the act of "generating an electromagnetic force"—whether explicitly discussed or not—and, conversely, were there effectively disclosure of the act of "generating an electromagnetic force", such a disclosure should be understood to encompass disclosure of an "electromagnetic force generator" and even a "means for generating an electromagnetic force." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the magnetically driven pressure generator herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A device comprising:
   a housing having a depth disposed between an open end and a closed end;
   a partition wall being configured to partition an enclosed space of said housing into a first fluid chamber and a second fluid chamber;
   a flexible member having a peripheral margin sealably engaged to an open end of said first fluid chamber, said flexible member being configured to flex to increase or decrease a volume of said enclosed space;
   a first magnetic force generator being disposed on said flexible member;
   a second magnetic force generator being disposed proximate said closed end of said housing or proximate said open end of said housing, said first magnetic force generator being responsive to said second magnetic force generator to flex said flexible member, at least one of said first magnetic force generator or said second magnetic force generator comprising an electromagnetic force generator being configured to flex said flexible member to increase or decrease said volume of said enclosed space;
   an aperture being disposed in said partition wall and being configured to permit fluid communication between said first fluid chamber and said second fluid chamber;
   a unidirectional valve being disposed in said partition wall and being configured to permit fluid flow through said aperture only from said second fluid chamber toward said first fluid chamber; and
   a cover being sealably engaged to an open end of said second fluid chamber.

2. The device of claim 1, further comprising a ferromagnetic core responsive to said second magnetic force generator, said ferromagnetic core generally axially aligned with said first magnetic force generator disposed on said flexible member.

3. The device of claim 1, wherein said electromagnetic force generator operable to intermittently flex said flexible member to increase or decrease said volume of said enclosed space, said electromagnetic force generator operates to oscillate said flexible member at a frequency of 0 kHz to 100 kHz.

4. The device of claim 3, wherein said enclosed space has a closed condition, and wherein flexing said flexible member to increase or decrease said volume of said enclosed space generates an amount of pressure in said enclosed space.

5. The device of claim 4, wherein said amount of pressure comprises a positive amount of pressure or a negative amount of pressure.

6. The device of claim 5, wherein said amount of pressure comprises 0 psi to 20 psi.

7. The device of claim 1, further comprising one or more ports communicating between opposite internal and external surfaces of said housing.

8. The device of claim 7, further comprising one or more tubular conduits correspondingly coupled to said one or more ports, said one or more tubular conduits operating to conduct a fluid into or out of said enclosed space.

9. The device of claim 8, wherein said one or more ports comprises a fluid outlet port, and wherein said one or more tubular conduits comprises a fluid delivery conduit engaged to said fluid outlet port, said fluid outlet port communicating between said external surface of said housing and said internal surface of said housing to conduct fluid out of said enclosed space.

10. The device of claim 9, wherein said one or more ports comprises pressure relief port coupled to a fluid pressure relief valve operable to release said amount of pressure in said enclosed space.

11. The device of claim 10, wherein said fluid pressure release valve operable to release said amount of pressure in said enclosed space in excess of 20 psi.

12. The device of claim 1 further comprising, a third magnetic force generator disposed proximate said closed end of said housing or proximate said open end of said housing, said first magnetic force generator responsive to said second magnetic force generator or said third magnetic force generator to flex said flexible member.

13. The device of claim 12, further comprising a ferromagnetic core responsive to said third electromagnetic force generator, said ferromagnetic core generally axially aligned with said first magnetic force generator disposed on said flexible member.

14. The device of claim 1 further comprising:
a fluid outlet port communicating between an external surface and an internal surface of the housing to conduct said fluid from said first fluid chamber; and
a fluid delivery conduit sealably engaged to said fluid outlet port for delivery of said fluid to a distal end of said fluid delivery conduit.

15. The device of claim 14 further comprising an earpiece coupled to said distal end of said fluid delivery conduit being configured to deliver said fluid into an external ear canal of an ear.

16. The device of claim 15 further comprising:
a fluid return conduit coupled to said earpiece through which said fluid flows from said external ear canal; and
a pressure release valve coupled to said fluid return conduit [[line ]]operable between an open condition which allows a flow of said fluid from said external ear canal and a closed condition which interrupts said flow of said fluid from said external ear canal.

17. The device of claim 16, further comprising a fluid inlet port communicating between said external surface and said internal surface of the housing to conduct said fluid into said second fluid chamber.

18. The device of claim 17, further comprising:
a fluid inlet conduit coupled to said fluid inlet port; and
a fluid source coupled to said fluid inlet conduit, said fluid source comprising fluid.

19. The device of claim 18, further comprising a fluid inlet valve disposed between said fluid inlet port and the fluid source, said fluid inlet valve being configured to interrupt fluid flow to said second fluid chamber.

20. The device of claim 19, further comprising a fluid bleed port communicating between said external surface of said housing and said internal surface of said housing to conduct said fluid into and out of said second fluid chamber.

21. The device of claim 20, further comprising a fluid flow generator coupled to said fluid bleed port, said fluid flow generator operatable to conduct said fluid into or out of said second fluid chamber.

22. The device of claim 21, further comprising a bleed valve operable in an open condition to allow egress of fluid out of said second fluid chamber.

23. The device of claim 22, further comprising:
a pressure sensor port communicating between said external surface of said housing and said internal surface of said housing of said first fluid chamber; and
a pressure sensor coupled to said pressure sensor port, said pressure sensor generates a signal which varies corresponding to an amount of pressure in said first fluid chamber.

24. The device of claim 23, further comprising a processor communicatively coupled to a non-transitory computer readable media comprising a computer program executable to control operation of a current controller.

25. The device of claim 24, wherein said current controller controls an amount of current delivered to said first electromagnetic force generator.

26. The device of claim 25, wherein said current controller further controls a direction of current flow in said first electromagnetic force generator.

27. The device of claim 26, wherein said computer program further executable to continuously or intermittently analyze said signal from said pressure sensor to determine divergence from a pre-selected pressure profile and correspondingly continuously or intermittently adjust said said amount of current or said direction of current flow to alter operation of said flexible member to compensate for said determined divergence from said pre-selected pressure profile.

* * * * *